(12) United States Patent
Knappe et al.

(10) Patent No.: US 9,211,425 B2
(45) Date of Patent: Dec. 15, 2015

(54) PRODUCT FOR KERATIN-CONTAINING FIBERS COMPRISING AT LEAST ONE SPECIFIC AMPHIPHILIC CATIONIC POLYMER, AND AT LEAST ONE SPECIFIC AMPHIPHILIC ANIONIC POLYMER

(75) Inventors: Thorsten Knappe, Schenefeld (DE); Marcus Noll, Norderstedt (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 61 days.

(21) Appl. No.: 13/027,492

(22) Filed: Feb. 15, 2011

(65) Prior Publication Data

US 2011/0135589 A1 Jun. 9, 2011

Related U.S. Application Data

(63) Continuation of application No. PCT/EP2009/059355, filed on Jul. 21, 2009.

(30) Foreign Application Priority Data

Aug. 18, 2008 (DE) .......................... 10 2008 038 105

(51) Int. Cl.
| | | |
|---|---|---|
| *A61Q 5/04* | (2006.01) | |
| *A61K 8/00* | (2006.01) | |
| *A61Q 5/06* | (2006.01) | |
| *A61K 8/81* | (2006.01) | |
| *A61K 8/86* | (2006.01) | |

(52) U.S. Cl.
CPC .............. *A61Q 5/06* (2013.01); *A61K 8/8182* (2013.01); *A61K 8/86* (2013.01); *A61K 2800/5424* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 3,753,968 A | 8/1973 | Ward | |
| 6,235,913 B1 | 5/2001 | Raths et al. | |
| 6,852,815 B1 | 2/2005 | Chuang et al. | |
| 7,332,466 B2 | 2/2008 | Schmid et al. | |
| 2004/0228809 A1* | 11/2004 | Birkel et al. | ..................... 424/47 |
| 2006/0013785 A1 | 1/2006 | Lauscher et al. | |
| 2006/0134049 A1* | 6/2006 | Keenan et al. | ............. 424/70.15 |
| 2007/0224140 A1* | 9/2007 | Quadir et al. | ................... 424/63 |
| 2007/0286833 A1* | 12/2007 | Keller et al. | ............... 424/70.11 |
| 2008/0119413 A1* | 5/2008 | Singer et al. | .................... 514/23 |
| 2009/0223531 A1* | 9/2009 | Lund et al. | .................... 132/208 |

FOREIGN PATENT DOCUMENTS

| | | |
|---|---|---|
| AU | 730455 B2 | 5/2000 |
| DE | 3139438 A1 | 4/1983 |
| DE | 19756454 C1 | 6/1999 |
| DE | 10240757 A1 | 7/2003 |
| DE | 102007008089 A1 | 8/2008 |

OTHER PUBLICATIONS

Cosmetic Science Technology, 2007, 142-156.*
"Aquastyle 300." ISP Corporation, Dec. 6, 2006, Retrieved from http://www.ispjapan.co.jp/pc_refguide/pdf/AquaStyle_300_jp, pp. 71, 92, on Dec. 3, 2009.
Rigoletto, Raymond et al. "Polyquaternium-69: A New Fixative Polymer with Enhanced Styling Benefits," Cosmetic Science Technology, Jan. 1, 2007, p. 142.
International Cosmetic Ingredient Dictionary & Handbook. The Cosmetic Toiletry and Fragrance Association, 7th Edition, 1997.

* cited by examiner

*Primary Examiner* — Snigdha Maewall
(74) *Attorney, Agent, or Firm* — Ingrassia Fisher & Lorenz, P.C.

(57) ABSTRACT

Product for treating keratin-containing fibers, especially human hair, comprising, in a cosmetically acceptable carrier: (a) at least one amphiphilic, cationic polymer, respectively comprising at least one structural unit of formulae (I) to (IV), wherein $R^1$ and $R^4$ are independently a hydrogen atom or a methyl group, X1 and X2 are independently an oxygen atom or an NH group, $A^1$ and $A^2$ are independently an ethane-1,2-diyl, propane-1,3-diyl or butane-1,4-diyl group, $R^2$, $R^3$, $R^5$ and $R^6$ are independently a (C1-C4)-alkyl group, and $R^7$ is a ($C_8$-$C_{30}$)-alkyl group, and (b) at least one amphiphilic anionic polymer, comprising at least one structural unit of formula (V) and at least one structural unit of formula (VI) wherein $R^8$ and $R^9$ are independently a hydrogen atom or a methyl group, $R^{10}$ is ($C_8$-$C_{30}$)-alkyl group, M+ is a physiologically compatible cation, and $A^3$ is a *—$(CH_2CH_2O)_x$—* group wherein x is a whole number between 5 and 35, a *—$(CH_2CHMeO)_y$—* group wherein y is a whole number between 5 and 35 or a *—$(CH_2CH_2O)_x$—$(CH_2CHMeO)_x$—* group wherein the sum of x+y is a whole number between 5 and 35, and x and y are higher than zero. The invention also relates to the use of said product for temporary hair styling and for hair care, especially in the form of a hair cream or a hair gel.

18 Claims, No Drawings

PRODUCT FOR KERATIN-CONTAINING FIBERS COMPRISING AT LEAST ONE SPECIFIC AMPHIPHILIC CATIONIC POLYMER, AND AT LEAST ONE SPECIFIC AMPHIPHILIC ANIONIC POLYMER

CROSS REFERENCE TO RELATED APPLICATIONS

The present application is a continuation of International Patent Application No. PCT/EP2009/059355 filed 21 Jul. 2009, which claims priority to German Patent Application No. 10 2008 038 105.5 filed 18 Aug. 2008, both of which are incorporated herein by reference.

The present invention relates to agents for treating hair having a combination of at least one specific amphiphilic, cationic polymer with at least one specific amphiphilic, anionic polymer, use of these agents for temporary shaping and/or for care of keratin-containing fibers, and hair gels based on these agents.

Keratin-containing fibers include all animal hair (e.g., wool, horsehair, angora hair, furs, feathers and products or fabrics produced from them). However, keratinic fibers preferably concern human hair.

Today, a suitably looking hairstyle is generally regarded as an essential part of a well groomed appearance. Based on actual fashion trends, time and again hairstyles are considered chic which, for many types of hair, can only be formed or sustained over a long period of up to several days by use of certain consolidating materials. Thus, hair treatments that provide a permanent or temporary hairstyling play an important role. Temporary styling that provides a good hold, without compromising the healthy appearance of the hair, such as gloss, can be obtained for example by use of hairsprays, hair waxes, hair gels, hair foams, setting lotions, etc.

Suitable compositions for temporary hairstyling usually contain synthetic polymers as the styling component. Preparations comprising a dissolved or dispersed polymer can be applied on hair by propellants or by a pumping mechanism. Hair gels and hair waxes, however, are not typically applied directly on the hair, but rather dispersed with a comb or by hand.

An important property of an agent for temporary styling of keratin fibers, also referred to as styling agents, involves giving the treated fibers the strongest possible hold for the created shape. If the keratinic fibers are human hair, then one also speaks of a strong hairstyle hold or a high degree of hold of the styling agent. Styling hold is basically determined by the type and quantity of synthetic polymer used, but other components of the styling agent may also influence the hold.

In addition to a high degree of hold, styling agents can fulfill a whole series of additional requirements. These requirements can be broadly divided into properties on the hair, properties of the formulation in question (e.g., properties of the foam, gel or aerosol spray), and properties concerning the handling of the styling agent, with particular importance attached to the properties on the hair. These include moisture resistance, low stickiness and a balanced conditioning effect. Furthermore, a styling agent should be universally applicable for as many types of hair as possible.

In an attempt to meet these diverse requirements, various synthetic polymers have been developed and are currently used in styling agents. These polymers can be divided into cationic, anionic, non-ionic and amphoteric film-forming and/or setting polymers. Ideally, these polymers form a polymer film when applied to hair, imparting a strong hold to the hairstyle while also being sufficiently flexible so as to not break under stress. If the polymer film is too brittle, film plaques can develop (i.e., residues that are shed with movement of the hair and give the impression that the user of the respective styling agent has dandruff).

When the styling agent is used in the form of a gel, it has proved advantageous to prepare it as a clear, transparent gel. The consumer perceives these clear gels as esthetically appealing, especially when gas bubbles are also incorporated in them. Unfortunately, it is often difficult to incorporate gas bubbles in conventional gel formulations. Even if gas bubbles were successfully incorporated into the conventional formulations, the gas bubbles would not be incorporated in a storage stable manner and would escape out of the gel.

To develop styling agents that have all the desired properties still presents problems. This particularly applies to the combination of aesthetic factors and strong and flexible hold. In order to impart a strong hold, the setting polymer has to adhere well to the keratin-containing fibers and form a sufficiently hard film. Still, the resulting polymer film should not impart the tactility of a board to the collective fibers, but rather give a degree of flexibility to the fibers without losing the marked styling of the collective fibers (i.e., a hair style).

Accordingly, the present invention provides an agent for temporary styling of keratinic fibers that has a very high degree of hold and does not form film plaques. Moreover, the agent is in the form of a clear, transparent gel, into which gas bubbles can be incorporated in a storage stable manner.

It has now been surprisingly found that this can be achieved by the inventive polymer combination discussed below. This polymer combination enables transparent gels to be manufactured into which gas bubbles can be permanently incorporated, wherein the resulting gels provide an excellent consolidation of the hair style.

Accordingly, a first subject matter of the present invention is agents for treating keratin-containing fibers, especially human hair, comprising in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

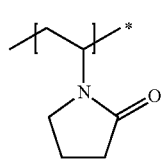
(I)

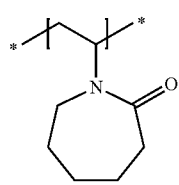
(II)

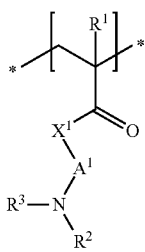

(III)

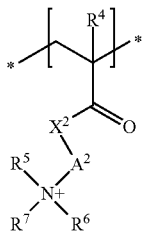

(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group; and (b) at least one amphiphilic, anionic polymer having at least one structural unit of Formula (V) and at least one structural unit of Formula (VI),

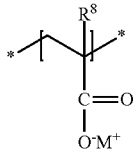

(V)

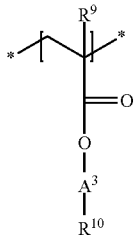

(VI)

wherein $R^8$ and $R^9$ are, independently of one another, a hydrogen atom or a methyl group, $R^{10}$ is a ($C_8$ to $C_{30}$) alkyl group, $M^+$ is a physiologically acceptable cation, and $A^3$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—*, wherein the sum of x+y is a whole number from 5 to 35 and x and y are greater than zero.

Exemplary inventive ($C_1$ to $C_4$) alkyl groups include methyl, ethyl, propyl, isopropyl, butyl, sec-butyl, isobutyl, tert-butyl.

Exemplary inventive ($C_8$ to $C_{30}$) alkyl groups include octyl (capryl), decyl (caprinyl), dodecyl (lauryl), tetradecyl (myristyl), hexadecyl (cetyl), octadecyl (stearyl), eicosyl (arachyl), docosyl (behenyl).

In the above Formulas and all Formulas below, the symbol * represents a chemical bond that stands for a free valence of the corresponding structural fragment.

To compensate for the positive polymer charge, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Metal cations of the physiologically acceptable metals of Groups Ia, Ib, IIa, IIb, IVb, VIa or VIII of the Periodic Table, ammonium ions, as well as cationic organic compounds containing a quaternized nitrogen atom are particularly suitable as the physiologically acceptable cations for compensating the negative charge of the amphiphilic, anionic polymer (b). Cationic organic compounds containing a quaternized nitrogen atom are formed, for example, by protonating primary, secondary or tertiary organic amines with an acid, or by permanent quaternization of the cited organic amines. These cationic organic ammonium compounds include 2-ammonioethanol and 2-trimethylammonioethanol.

Properties of the agent prove to be particularly advantageous when it is in the form of a cream, preferably in the form of a gel, especially in the form of a clear, transparent gel. This preferred packaging form is described later in detail.

The following amphiphilic, cationic polymers are preferably employed in agents according to the invention when the amphiphilic, cationic polymers fulfill one or more of the following criteria:

$R^1$ and $R^4$ are each a methyl group, $X^1$ is an NH group, $X^2$ is an NH group, $A^1$ and $A^2$ are, independently of one another, ethane-1,2-diyl or propane-1,3-diyl, $R^2$, $R^3$, $R^5$ and $R^6$ are, independently of one another, methyl or ethyl, (preferably methyl), $R^7$ is a ($C_{10}$ to $C_{24}$) alkyl group, especially decyl (caprinyl), dodecyl (lauryl), tetradecyl (myristyl), hexadecyl (cetyl), octadecyl (stearyl), eicosyl (arachyl) or docosyl (behenyl).

Preferably, the structural unit of Formula (III) is chosen from at least one of the structural units of Formula (III-1) to (III-8)

(III-1)

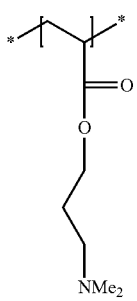 (III-2)

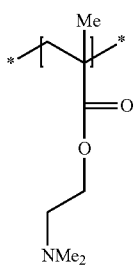 (III-3)

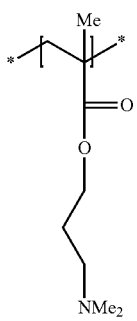 (III-4)

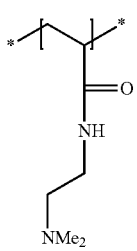 (III-5)

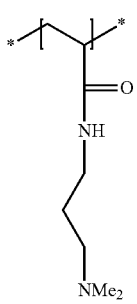 (III-6)

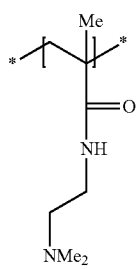 (III-7)

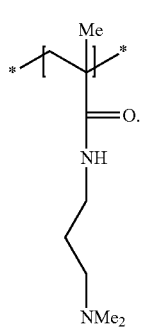 (III-8)

Moreover, it has proven particularly preferable to choose the structural unit according to Formula (III-7) and/or of Formula (III-8) as the structural unit of Formula (III). According to the invention, the structural unit of Formula (III-8) is a quite particularly preferred structural unit.

Furthermore, the structural unit of Formula (IV) is preferably chosen from at least one structural unit of Formulas (IV-1) to (IV-8)

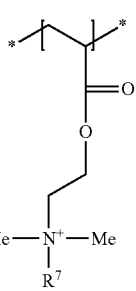 (IV-1)

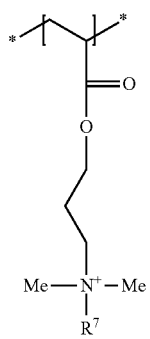 (IV-2)

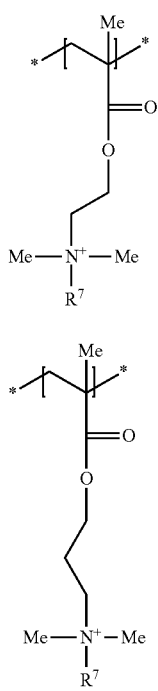

(IV-3)

(IV-4)

(IV-5)

(IV-6)

(IV-7)

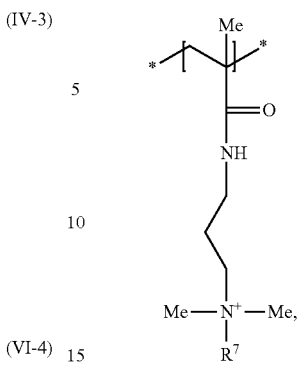

(VI-8)

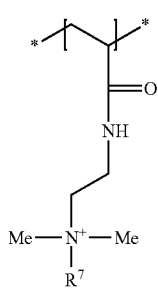

wherein each $R^7$ is a ($C_8$ to $C_{30}$) alkyl group.

The structural units of Formula (IV-7) and/or of Formula (IV-8) are particularly preferred as the structural unit of Formula (IV), wherein each $R^7$ is octyl (capryl), decyl (caprinyl), dodecyl (lauryl), tetradecyl (myristyl), hexadecyl (cetyl), octadecyl (stearyl), eicosyl (arachyl) oder docosyl (behenyl). According to the invention, the structural unit of Formula (IV-8) is a quite particularly preferred structural unit of Formula (IV).

A quite particularly preferred amphiphilic, cationic polymer contains at least one structural unit of Formula (I), at least one structural unit of Formula (II), at least one structural unit of Formula (III-8), and at least one structural unit of Formula (IV-8),

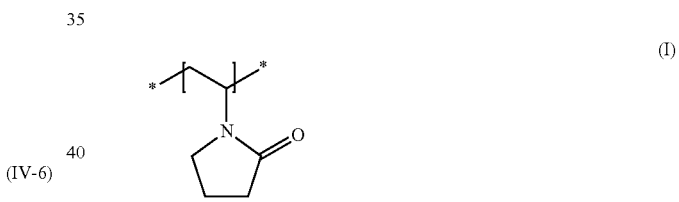

(I)

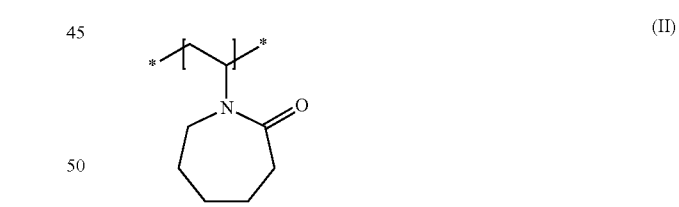

(II)

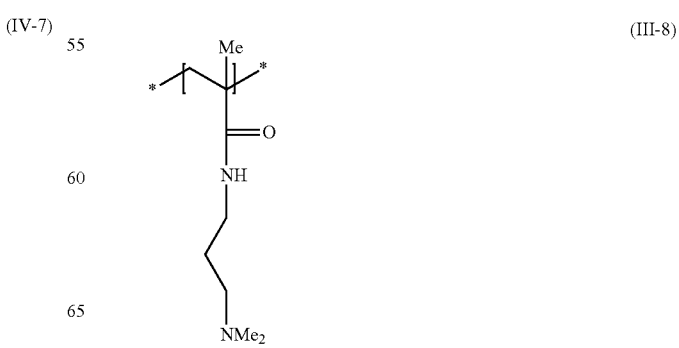

(III-8)

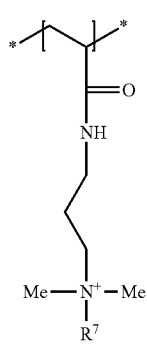

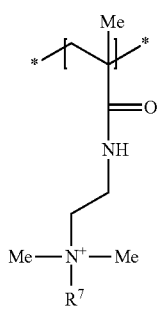

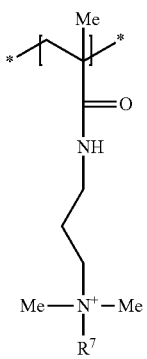

(IV-8)

wherein $R^7$ is a ($C_8$ to $C_{30}$) alkyl group, especially octyl (capryl), decyl (caprinyl), dodecyl (lauryl), tetradecyl (myristyl), hexadecyl (cetyl), octadecyl (stearyl), eicosyl (arachyl) or docosyl (behenyl).

Molecular weights of amphiphilic, cationic polymers according to the invention are preferably from 10,000 g/mol to 50,000,000 g/mol, more preferably from 50,000 g/mol to 5,000,000 g/mol, particularly preferably from 75,000 g/mol to 1,000,000 g/mol.

A quite particularly preferred amphiphilic, cationic polymer is the copolymer of N-vinyl pyrrolidone, N-vinyl caprolactam, N-(3-dimethylaminopropyl)methacrylamide and 3-(methacryloylamino)propyl-lauryl-dimethylammonium chloride (INCI name: Polyquaternium-69), marketed, for example, by the ISP company under the trade name AquaStyle® 300 (28-32 wt. % active substance in an ethanol-water mixture).

According to the invention, preferred agents contain the above described amphiphilic, cationic polymers preferably in an amount of 0.05 wt. % to 15.0 wt. %, more preferably 0.05 wt. % to 10.0 wt. %, particularly preferably 0.1 wt. % to 5.0 wt. %, based on total weight of the agent.

The agent further includes, in addition to the previously defined amphiphilic, cationic polymer, at least one previously defined amphiphilic, anionic polymer.

These amphiphilic, anionic polymers can be crosslinked or uncrosslinked. According to the invention, "crosslinked" or "crosslinking" refers to the linkage of polymer chains with one another through covalent chemical bonding with the formation of a network. This covalent linkage of the polymer chains can result from direct covalent bonds or be imparted by a molecular fragment connecting the polymer chains together. The molecular fragment bonds to each of the polymer chains connected by the molecular fragment by a covalent chemical bond. According to the invention, "uncrosslinked" means that no previously defined "crosslinking" exists. Crosslinking of the crosslinked embodiment of the amphiphilic, anionic polymers (b) can preferably be effected by use of at least one crosslinking monomer. In this regard it is again preferred to choose the crosslinking monomer from at least one compound of polyunsaturated aromatic monomers (such as divinylbenzene, divinylnaphthalene, trivinylbenzene), polyunsaturated alicyclic monomers (such as 1,2,4-trivinylcyclohexane), di-functional esters of phthalic acid (such as diallyl phthalate), polyunsaturated aliphatic monomers (such as dienes, trienes, tetraenes such as isoprene, 1,3-butadiene, 1,5-hexadiene, 1,5,9-decatriene, 1,9-decadiene, 1,5-heptadiene), polyalkenyl ethers (such as triallyl pentaerythritol, diallyl pentaerythritol, diallyl sucrose, octaallyl sucrose, trimethylolpropane diallyl ether), polyunsaturated esters of polyalcohols or polyacids (such as 1,6-hexane diol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate), alkylene bisacrylamides (such as methylene bisacrylamide, propylene bisacrylamide) hydroxy and carboxy derivatives of methylene bisacrylamide (such as N,N'-bismethylolmethylene bisacrylamide), polyethylene glycol di(meth)acrylates (such as ethylene glycol di(meth)acrylate, diethylene glycol di(meth)acrylate, triethylene glycol di(meth)acrylate), polyunsaturated silanes (such as dimethyldivinylsilane, methyltrivinylsilane, allyldimethylvinylsilane, diallyldimethylsilane, tetravinylsilane), N-methylolacrylamide; N-alkoxy (meth)acrylamides, wherein the alkoxy group is a ($C_1$ to $C_{18}$) alkoxy group, unsaturated hydrolyzable silanes (such as triethoxy vinylsilane, trisisopropoxy vinylsilane, 3-triethoxy silylpropylmethacrylate), hydrolyzable silanes (such as ethyltriethoxysilane, ethyltrimethoxysilane), epoxy-substituted hydrolyzable silanes (such as 2-(3,4-epoxycyclohexypethyl-triethoxysilane, 3-glycidoxypropyltrimethoxysilane) polyisocyanates (such as 1,4-diisocyanatobutane, 1,6-diisocyanatohexane, 1,4-phenylenediisocyanate, 4,4'-oxybis (phenylisocyanate), unsaturated epoxides (such as glycidyl methacrylate, allyl glycidyl ether), polyepoxides (such as diglycidyl ether, 1,2,5,6-diepoxyhexane, ethylene glycol diglycidyl ether), ethoxylated polyols (such as diols, triols and diphenols, each ethoxylated with 2 to 100 mol ethylene oxide per mol hydroxyl groups and terminated with a polymerizable unsaturated group, such as vinyl ether, allyl ether, acrylate ester, methacrylate ester; for example, including ethoxylated Bisphenol A di(meth)acrylate, ethoxylated Bisphenol F di(meth)acrylate, ethoxylated trimethylolpropane tri(meth) acrylate, acrylate and methacrylate esters of polyols with at least two acrylate ester or methacrylate ester functionalities (such as trimethylolpropane triacrylate (TMPTA), trimethylolpropane ethoxylated (15) triacrylate (TMPEO15TA), trimethylolpropane dimethacrylate, triethylene glycol dimethacrylate (TEGDMA), Bisphenol A dimethacrylate ethoxylated with 30 mol ethylene oxide (EOBDMA)).

Agents are particularly preferred wherein the molecular mass of the amphiphilic, anionic polymers (b) is from 100 to 500 kDa, preferably from 150 to 400 kDa, more preferably from 200 to 300 kDa and particularly from 225 to 275 kDa.

According to the invention, preferred agents contain amphiphilic, anionic polymers (b) in an amount of 0.05 wt. % to 10.0 wt. %, particularly preferably 0.05 wt. % to 5.0 wt. %, quite particularly preferably 0.1 wt. % to 2.0 wt. %, based on total weight of the agent.

Polymers (a) and (b) are preferably employed in a weight ratio [polymer (a) to polymer (b)] of 1 to 10 to 10 to 1, more preferably 1 to 5 to 5 to 1, quite preferably 1 to 3.5 to 3.5 to 1.

Preferably, amphiphilic, anionic polymers (b) are chosen from copolymers b1 having at least one structural unit of Formula (V-1), at least one structural unit of Formula (V-2), and at least one structural unit of Formula (VI)

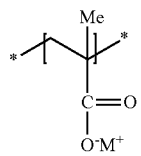

(V-1)

-continued

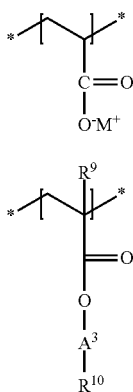
(V-2)
(VI)

wherein
M⁺ are, independently of one another, a physiologically acceptable cation,
$R^9$ is a hydrogen atom or a methyl group (preferably a methyl group),
$R^{10}$ is a ($C_8$ to $C_{30}$) alkyl group, especially octyl (capryl), decyl (caprinyl), dodecyl (lauryl), tetradecyl (myristyl), hexadecyl (cetyl), octadecyl (stearyl), eicosyl (arachyl) or docosyl (behenyl), and
$A^3$ is *—$(CH_2CH_2O)_x$—* wherein x is a whole number from 5 to 35, *—$(CH_2CHMeO)_y$—* wherein y is a whole number from 5 to 35 or a group, *—$(CH_2CH_2O)_x$—$(CH_2CHMeO)_y$—* wherein the sum x+y is a whole number from 5 to 35, and x and y are greater than zero (preferably *—$(CH_2CH_2O)_x$—* wherein x is a whole number from 5 to 30).

Preferably, copolymers b1 have at least one structural unit of Formula (V-1), at least one structural unit of Formula (V-2) and at least one structural unit of Formula (VI-1)

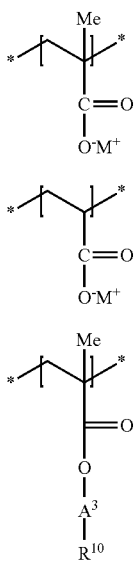
(V-1)
(V-2)
(VI-1)

wherein
M⁺ are, independently of one another, a physiologically acceptable cation,
$R^{10}$ is a ($C_8$ to $C_{30}$) alkyl group (especially octyl (capryl), decyl (caprinyl), dodecyl (lauryl), tetradecyl (myristyl), hexadecyl (cetyl), octadecyl (stearyl), eicosyl (arachyl) or docosyl (behenyl)), and $A^3$ is *—$(CH_2CH_2O)_x$—* wherein x is a whole number from 5 to 35, particularly from 15 to 30 (15, 16, 17, 18, 19, 20, 21, 22, 23, 24, 25, 26, 27, 28, 29, 30).

For clarity, according to Formula (VI) or (VI-1), the group $R^{10}$ always bonds to the oxygen atom of the group $A^3$.

Those amphiphilic, anionic polymers (b) are again preferably employed which are chosen from copolymers b1 of acrylic acid with methacrylic acid, at least one ($C_1$ to $C_4$) alkyl acrylate and at least one ethoxylated methacrylic acid ester and/or ethoxylated acrylic acid ester.

These copolymers b1 can be described by Formula (b1-1)

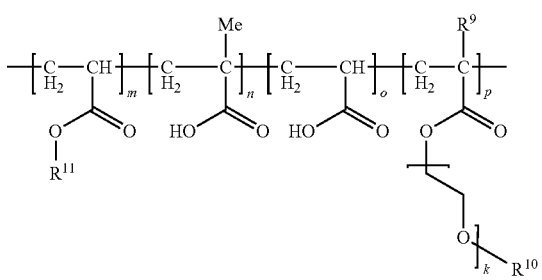
(b1-1)

wherein indices m, n, o and p each vary with the molecular mass of the polymer,
$R^9$ is a hydrogen atom or a methyl group,
$R^{10}$ is a hydrocarbon group containing 8 to 30 carbon atoms, especially 10 to 24 carbon atoms,
$R^{11}$ is a ($C_1$ to $C_4$) alkyl group (preferably —$CH_3$, —$CH_2CH_3$, —$CHMe_2$, —$CH_2CH_2CH_3$, —$CH_2CHMeCH_3$ or —$CH_2CH_2CH_2CH_3$, quite particularly preferably —$CH_3$ and/or —$CH_2CH_3$), and
x is a number from 5 to 35 (especially 15 to 30).

The arrangement of the structural units in the above Formula (b1-1) does not imply that copolymers b1 are necessarily block copolymers. In fact, the structural units can be statistically distributed in the molecule.

Particularly preferred inventive agents contain copolymers of ($C_1$ to $C_4$) alkyl acrylate, acrylic acid, methacrylic acid and ethoxylated (meth)acrylic acid esters as the copolymer b1 having a molecular mass of 100 to 500 kDa, preferably 150 to 400 kDa, more preferably 200 to 300 kDa and particularly 225 to 275 kDa. Indices m, n, o and p correspond to those of the embodiment of the Formula (b1-1).

The preferred quantity ranges in which the preferred copolymer b1 is employed in the agent, as well as the quantities of amphiphilic, cationic polymer (a) and the quantity ratios to amphiphilic, cationic polymer (a) correspond to the previous statements (see above).

Particularly preferred copolymers b1 contain 20 to 30 EU units (x=20, 21, 22, 23, 24, 25, 26, 27, 28, 29, 30) and have a stearyl group or behenyl group as the R group.

A quite particularly preferred amphiphilic, anionic polymer (b) has 25 EO units, is esterified with behenyl alcohol, and is named according to INCI nomenclature as Acrylates/Beheneth-25 Methacrylate Copolymer. A polymer of this type is available, for example, under the trade name Aculyn® 28 (Rohm & Haas).

A quite particularly preferred polymer (b) is a crosslinked, amphiphilic, anionic polymer that falls under the INCI name Acrylates/Steareth-20 Methacrylate Crosspolymer. It has 20 ethylene oxide units (x according to Formula (VI-1)=20) and is etherified with stearyl alcohol ($R^{10}$ according to Formula (VI-1)=Stearyl). Polymers of this type are marketed, for example, by Rohm & Haas under the trade name Aculyn® 88 in the form of a 28 to 30 wt. % conc. dispersion in water.

A particularly preferred agent, especially in the form of a gel, comprises in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

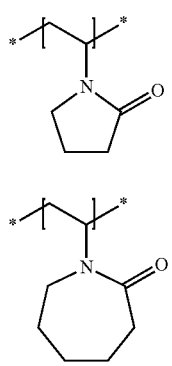

(I)

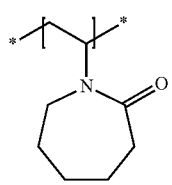

(II)

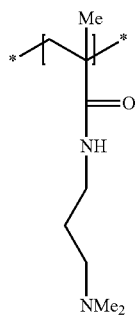

(III-8)

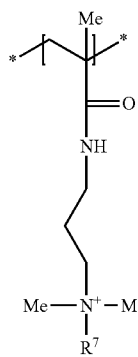

(IV-8)

wherein $R^7$ is a ($C_8$ to $C_{30}$) alkyl group (especially octyl (capryl), decyl (caprinyl), dodecyl (lauryl), tetradecyl (myristyl), hexadecyl (cetyl), octadecyl (stearyl), eicosyl (arachyl) or docosyl (behenyl)), and (b) at least one amphiphilic, anionic polymer having at least one structural unit of Formula (V-1), at least one structural unit of Formula (V-2), and at least one structural unit of Formula (VI-1)

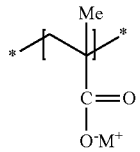

(V-1)

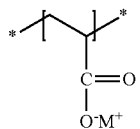

(V-2)

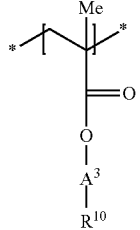

(VI-1)

wherein $M^+$ are, independently of one another, a physiologically acceptable cation, $R^{10}$ is a ($C_8$ to $C_{30}$) alkyl group (especially octyl (capryl), decyl (caprinyl), dodecyl (lauryl), tetradecyl (myristyl), hexadecyl (cetyl), octadecyl (stearyl), eicosyl (arachyl) or docosyl (behenyl)), and $A^3$ is a *—$(CH_2CH_2O)_x$—* wherein x is a whole number from 5 to 35, especially from 15 to 30 (15, 16, 17, 18, 19, 20, 21, 22, 23, 24, 25, 26, 27, 28, 29, 30).

A quite particularly preferred agent, especially in the form of a gel, comprises in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

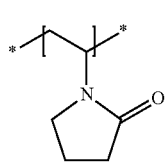

(I)

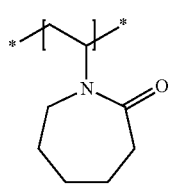

(II)

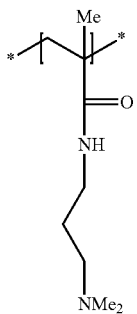

(III-8)

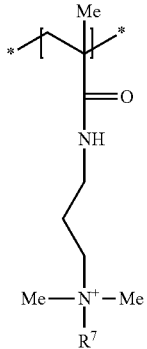

(IV-8)

wherein $R^7$ is a ($C_8$ to $C_{30}$) alkyl group (especially octyl (capryl), decyl (caprinyl), dodecyl (lauryl), tetradecyl (myristyl), hexadecyl (cetyl), octadecyl (stearyl), eicosyl (arachyl) or docosyl (behenyl)), and (b) at least one amphiphilic, anionic polymer of the Formula (b1-1)

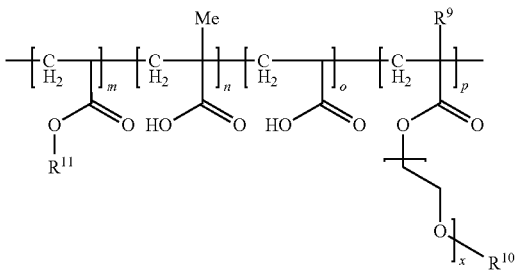

(b1-1)

wherein indices in, n, o and p are each a whole number greater than zero, $R^9$ is a hydrogen atom or a methyl group, $R^{10}$ is a hydrocarbon group containing one to 24 carbon atoms, $R^{11}$ is a ($C_1$ to $C_4$) alkyl group (preferably —$CH_3$, —$CH_2CH_3$, —$CHMe_2$, —$CH_2CH_2CH_3$, —$CH_2CHMeCH_3$ or —$CH_2CH_2CH_2CH_3$, more preferably —$CH_3$ and/or —$CH_2CH_3$), x is a number from 5 to 35 (especially 15 to 30).

Arrangement of the structural units in the above Formula (b1-1) does not imply that copolymers b1 are necessarily block copolymers. In fact, the structural units can be statistically distributed in the molecule.

In the context of the abovementioned particularly or quite particularly preferred agents, it is again preferred when the amphiphilic, anionic polymers (b) or (b1-1) are crosslinked.

In a preferred embodiment, the agent further comprises, in addition to the amphiphilic, cationic polymer (a) and amphiphilic, anionic polymer (b), additionally at least one film-forming and/or setting polymer (c). This last polymer (c) differs from polymers (a) and (b).

Preferred properties of the film-forming polymers include film formation. Film-forming polymers refer to those polymers that, on drying, leave a continuous film on the skin, hair or nails. These types of film-formers can be used in a wide variety of cosmetic products such as make up masks, make up, hair sets, hair sprays, hair gels, hair waxes, hair conditioners, shampoos or nail varnishes. Those polymers which are sufficiently soluble in alcohol or water/alcohol mixtures, so that they are present in completely dissolved form in the agents, are particularly preferred. Film-forming polymers can be of synthetic or of natural origin.

According to the invention, film-forming polymers further refer to those polymers that, when used in concentrations of 0.1 to 20 wt. % in aqueous, alcoholic or aqueous alcoholic solution, are able to separate out a transparent polymer film on the hair.

Setting polymers contribute to the hold and/or creation of hair volume and hair body of the whole hairstyle. These polymers are also film-forming polymers, and therefore are generally typical substances for styling hair treatment compositions such as hair sets, hair foams, hair waxes, hair sprays. Film formation can be in completely selected areas and bond only some fibers together.

The curl-retention test is frequently used as a test method for the setting action.

As polymers are often multifunctional (i.e., show a plurality of desired end-use effects), a large number of polymers are to be found in many of the groups subdivided according to the mode of action, therefore also in the CTFA Handbook.

The agent preferably has at least one film-forming and/or setting polymer chosen from at least one polymer of non-ionic polymers, cationic polymers, amphoteric polymers, zwitterionic polymers and anionic polymers.

The agent preferably has additional film-forming and/or setting polymers in an amount of 0.01 wt. % to 20.0 wt. %, particularly preferably 0.5 wt. % to 15.0 wt. %, quite particularly preferably 2.0 wt. % to 10.0 wt. %, based on total weight of the agent. These quantitative data also apply for all subsequent preferred types of film-forming and/or setting polymers that can be used in the inventive agents. When subsequently different preferred quantities were specified, then the latter are to be taken as the preferred quantities.

Those agents are particularly suitable that have, besides the previously defined amphiphilic, cationic polymers, at least one film-forming and/or setting polymer chosen from at least one polymer of the group consisting of non-ionic polymers based on ethylenically unsaturated monomers, especially from
  homopolymers of N-vinyl pyrrolidone, non-ionic copolymers of N-vinyl pyrrolidone,
  homopolymers and non-ionic copolymers of N-vinyl caprolactam,
  copolymers of (meth)acrylamide, polyvinyl alcohol, polyvinyl acetate,
chitosan and derivatives of chitosan,
cationic cellulose derivatives,
cationic copolymers of 3-($C_1$ to $C_6$)-alkyl-1-vinyl-imidazolinium,
homopolymers and copolymers comprising the structural unit of the Formula (M-1)

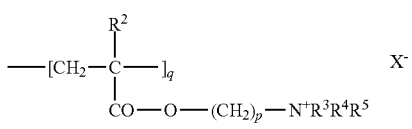 (M-1)

wherein R² =—H or —CH₃, R³, R⁴ and R⁵ are, independently of each other, chosen from ($C_1$ to $C_4$) alkyl, ($C_1$ to $C_4$) alkenyl or ($C_2$ to $C_4$) hydroxyalkyl groups, p=1, 2, 3 or 4, q is a natural number and X— is a physiologically acceptable organic or inorganic anion, anionic polymers that exhibit carboxylate and/or sulfonate groups, and anionic polyurethanes.

Preferred non-ionic polymers based on ethylenically unsaturated monomers suitable as the film-forming and/or setting polymers are those non-ionic polymers having at least one of the following structural units

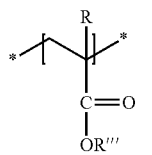 (M2)

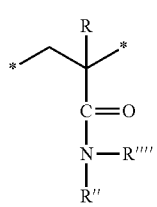 (M3)

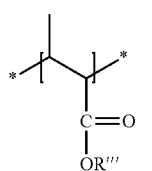 (M4)

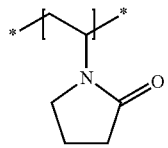 (M5)

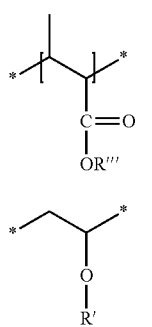 (M6)

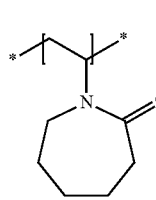 (M7)

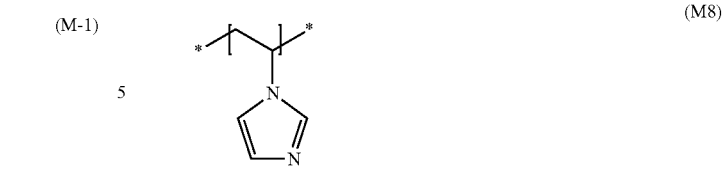 (M8)

wherein
R is a hydrogen atom or a methyl group,
R' is a hydrogen atom or a ($C_1$ to $C_4$) acyl group,
R" and R"" are, independently of one another, a ($C_1$ to $C_7$) alkyl group or a hydrogen atom, and
R'" is for a linear or branched ($C_1$ to $C_4$) alkyl group or a ($C_2$ to $C_4$) hydroxyalkyl group.

Suitable, non-ionic film-forming and/or non-ionic hair setting polymers are homopolymers or copolymers based on at least one of the following monomers: vinyl pyrrolidone, vinyl caprolactam, vinyl esters such as vinyl acetate, vinyl alcohol, acrylamide, methacrylamide, alkyl and dialkyl acrylamide, alkyl and dialkyl methacrylamide, alkyl acrylate, alkyl methacrylate, wherein each alkyl group of these monomers is chosen from ($C_1$ to $C_3$) alkyl groups.

For agents according to the invention, particularly suitable non-ionic polymers based on ethylenically unsaturated monomers have at least one of the following structural units

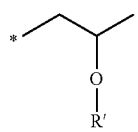 (M5)

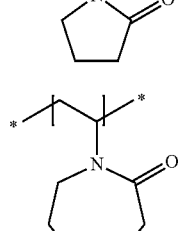 (M6)

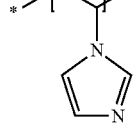 (M7)

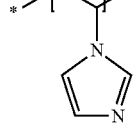 (M8)

wherein R' is a hydrogen atom or a ($C_1$- to $C_{30}$) acyl group, particularly a hydrogen atom or an acetyl group.

Homopolymers of vinyl caprolactam or vinyl pyrrolidone (such as Luviskol® K 90 or Luviskol® K 85 from BASF SE), copolymers of vinyl pyrrolidone and vinyl acetate (such as are marketed by BASF SE under the trade names Luviskol® VA 37, Luviskol® VA 55, Luviskol® VA 64 and Luviskol® VA 73), terpolymers of vinyl pyrrolidone, vinyl acetate and vinyl propionate, polyacrylamides (such as Akypomine® P 191 from CHEM-Y), polyvinyl alcohols (marketed, for example, under the trade names Elvanol® by Du Pont or Vinol® 523/540 by Air Products), terpolymers of vinyl pyrrolidone, methacrylamide and vinyl imidazole (such as Luviset® Clear from BASF SE) are particularly suitable.

In addition to non-ionic polymers based on ethylenically unsaturated monomers, non-ionic cellulose derivatives are also suitable film-forming and/or setting polymers. They are preferably chosen from methyl cellulose. especially from cellulose ethers such as hydroxypropyl cellulose (e.g., hydroxypropyl cellulose with a molecular weight of 30,000 to 50,000 g/mol, marketed, for example, under the trade name Nisso SI® by Lehmann & Voss, Hamburg), hydroxyethyl celluloses, such as are marketed under the trade names Culminal® and Benecel® (AQUALON) and Natrosol® types (Hercules).

Cationic polymers refer to polymers that have, in their main chain and/or side chain, groups that can be "temporarily" or "permanently" cationic. "Permanently cationic" refers to those polymers which, independently of the pH of the medium, have a cationic group. These are, for example, typically polymers having a quaternary nitrogen atom in the form of an ammonium group. Preferred cationic groups are quaternary ammonium groups. In particular, those polymers wherein the quaternary ammonium groups are bonded through a $C_{1-4}$ hydrocarbon group to a polymer backbone formed from acrylic acid, methacrylic acid or their derivatives have proved to be particularly suitable.

Copolymers of quaternized derivatives of dialkylaminoalkyl (meth)acrylate and/or copolymers of quaternized derivatives of dialkylaminoalkyl (meth)acrylamide are particularly preferred suitable cationic film-forming and/or cationic setting polymers.

Copolymers with monomer units according to formula (M1) preferably include acrylamide, methacrylamide, $C_{1-4}$ alkyl esters of acrylic acid and $C_{1-4}$ alkyl esters of methacrylic acid as the non-ionic monomer units. Acrylamide is particularly preferred among these non-ionic monomers. These copolymers can also be crosslinked, as in the above described homopolymers. An inventively preferred copolymer is the crosslinked acrylamide/methacryloyloxyethyltrimethylammonium chloride copolymer. Such copolymers, wherein the monomers are present in a weight ratio of about 20:80, are commercially available as a ca. 50% conc. non-aqueous polymer dispersion named Salcare® SC 92.

A further inventively preferred suitable cationic film-forming and/or cationic setting polymer is at least one cationic film-forming and/or cationic setting polymer having at least one structural element of Formula (M9) as well as at least one structural element of Formula (M10)

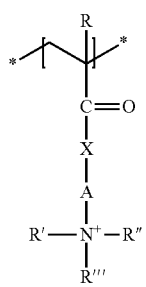

(M9)

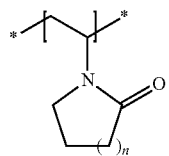

(M10)

wherein
R is a hydrogen atom or a methyl group,
R', R" and R'" are, independently of one another, a ($C_1$ to $C_{30}$) alkyl group,
X is an oxygen atom or an NH group,
A is an ethane-1,2-diyl group or a propane-1,3-diyl group,
n is 1 or 3.

To compensate for the positive polymer charge, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Such compounds include copolymers of
dimethylaminoethyl methacrylate, quaternized with diethyl sulfate, with vinyl pyrrolidone having the INCI name Polyquaternium-11, available under the trade names Gafquat® 440, Gafquat® 734, Gafquat® 755 (each from ISP) and Luviquat PQ 11 PN (BASF SE).

Furthermore, the cationic film-forming and/or cationic setting polymers are preferably chosen from cationic, quaternized cellulose derivatives.

Moreover, cationic, quaternized cellulose derivatives are preferred suitable film-forming and/or setting polymers.

Those cationic, quaternized celluloses having more than one permanent cationic charge in a side chain have proven to be particularly advantageous. Among these cationic celluloses, those with the INCI name Polyquaternium-4 are particularly suitable, marketed, for example, by the National Starch Company under the trade names Celquat® H 100, Celquat® L 200.

According to the invention, those cationic film-forming and/or cationic setting copolymers having at least one structural element according to Formula (M11) additionally serve as particularly preferred usable cationic polymers

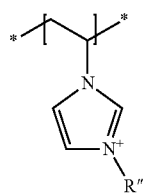

(M11)

wherein R" is a ($C_1$ to $C_4$) alkyl group, particularly a methyl group, and additionally having at least one further cationic and/or non-ionic structural element.

To compensate for the positive polymer charge, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Preferably, at least one copolymer (d) further contains, in addition to at least one structural element of Formula (M11), a structural element of Formula (M6) and is the additional cationic film-forming and/or cationic setting polymer

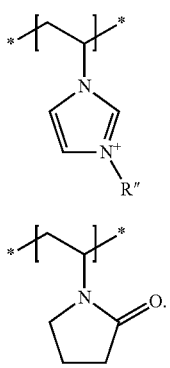
(M11)

(M6)

wherein R″ is a ($C_1$ to $C_4$) alkyl group, particularly a methyl group.

To compensate for the positive polymer charge of copolymer (c1), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Cationic film-forming and/or cationic setting polymers that are quite particularly preferred as copolymers (c1) have 10 to 30 mol %, preferably 15 to 25 mol % and particularly 20 mol % of structural units according to Formula (M11) and 70 to 90 mol %, preferably 75 to 85 mol % and particularly 80 mol % of structural units according to Formula (M6).

In this regard, it is particularly preferred when copolymers (c1) have, in addition to polymer units resulting from the incorporation of the cited structural units according to Formula (M11) and (M6) into the copolymer, a maximum of 5 wt. %, preferably a maximum of 1 wt. % of polymer units that trace back to the incorporation of other monomers. Copolymers (c1) are preferably exclusively formed from structural units of Formula (M11) with R″=methyl and (M6), and can be described by the general Formula (Poly1)

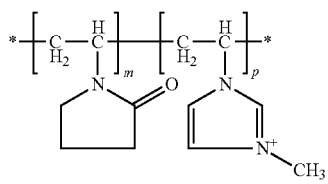
(Poly1)

wherein indices m, and p vary according to the molecular mass of the polymer and are not intended to mean to portray block copolymers. In fact, structural units of Formula (M11) and Formula (M6) can be statistically distributed in the molecule.

If a chloride ion is used to compensate the positive charge of the polymer of Formula (Poly1), then these N-methyl vinylimidazole/vinyl pyrrolidone copolymers named according to INCI nomenclature as Polyquaternium-16 and are available, for example, from BASF under the trade names Luviquat® Style, Luviquat® FC 370, Luviquat® FC 550, Luviquat® FC 905 and Luviquat® HM 552.

If a methosulfate ion is used to compensate the positive charge of the polymer of Formula (Poly1), then these N-methyl vinylimidazole/vinyl pyrrolidone copolymers named according to INCI nomenclature as Polyquaternium-44 and are available from, for example, BASF under the trade name Luviquat® UltraCare.

Particularly preferred inventive agents contain a copolymer (c1), especially of Formula (Poly1), having molecular masses within a defined range. Here, agents are preferred wherein the molecular mass of copolymer (c1) is from 50 to 400 kDa, preferably from 100 to 300 kDa, more preferably from 150 to 250 kDa and particularly from 190 to 210 kDa.

In addition to copolymer(s) (c1) or instead of it or them, the agents can also include copolymers (c2) that, starting from copolymer (c1), have as additional structural units structural units of Formula (M7)

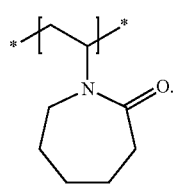
(M7)

Further particularly preferred agents are those having as the cationic film-forming and/or cationic setting polymer at least one copolymer (c2) having at least one structural unit according to Formula (M11-a), at least one structural unit according to Formula (M6), and at least one structural unit according to Formula (M7)

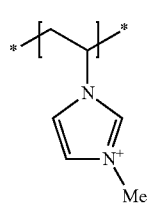
(M11-a)

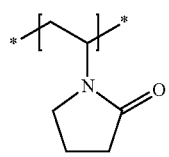
(M6)

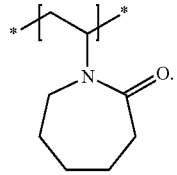
(M7)

Also, it is particularly preferred when copolymers (c2) have, in addition to polymer units due to the incorporation of the cited structural units according to Formula (M11-a), (M6) and (M7) into the copolymer, a maximum of 5 wt. %, preferably a maximum of 1 wt. % of polymer units that trace back to the incorporation of other monomers. Copolymers (c2) are preferably exclusively formed from structural units of Formula (M11-a), (M6) and (M7) and can be described by the general Formula (Poly2)

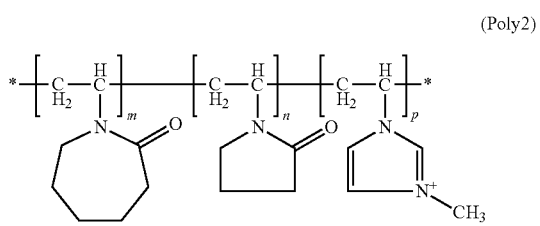

(Poly2)

wherein indices m, n and p vary according to the molecular mass of the polymer and are not intended to mean to portray block copolymers. In fact, structural units of the cited Formulas can be statistically distributed in the molecule.

To compensate for the positive polymer charge of the component (c2), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate the positive charge of the polymer of Formula (Poly2), then these N-methyl vinylimidazole/vinyl pyrrolidone/vinyl caprolactam copolymers named according to INCI nomenclature as Polyquaternium-46 and are available from for example BASF under the trade name Luviquat® Hold.

Quite particularly preferred copolymers (c2) have 1 to 20 mol %, preferably 5 to 15 mol % and particularly 10 mol % of structural units according to Formula (M11-a), 30 to 50 mol %, preferably 35 to 45 mol % and particularly 40 mol % of structural units according to Formula (M6), and 40 to 60 mol %, preferably 45 to 55 mol % and particularly 60 mol % of structural units according to Formula (M7).

Particularly preferred agents have a copolymer (c2) that has molecular masses within a defined range. Here, agents are preferred wherein the molecular mass of the copolymer (c2) is from 100 to 1000 kDa, preferably from 250 to 900 kDa, more preferably from 500 to 850 kDa and particularly from 650 to 710 kDa.

In addition to copolymer(s) (c1) and/or (c2) or in its or their place, the agents can also have copolymers (c3) as the film-forming cationic and/or setting cationic polymer which has as structural units structural units of the Formulas (M11-a) and (M6), as well as structural units from the group of vinyl imidazole units and further structural units from the group of acrylamide and/or methacrylamide units.

Further particularly preferred agents according to the invention have as the additional cationic film-forming and/or cationic setting polymer at least one copolymer (c3) having at least one structural unit according to Formula (M11-a), at least one structural unit according to Formula (M6), at least one structural unit according to Formula (M10), and at least one structural unit according to Formula (M12)

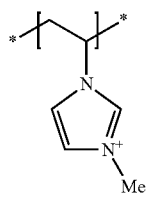

(M11-a)

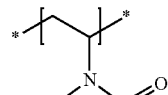

(M6)

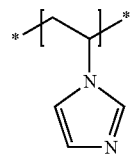

(M8)

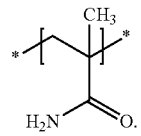

(M12)

Also, it is particularly preferred when copolymers (c3) have, in addition to polymer units resulting from the incorporation of the cited structural units according to Formulae (M11-a), (M6), (M8) and (M12) into the copolymer, a maximum of 5 wt. %, preferably a maximum of 1 wt. % of polymer units that trace back to the incorporation of other monomers. Copolymers (c3) are preferably exclusively formed from structural units of Formulae (M11-a), (M6), (M8) and (M12) and can be described by general Formula (Poly3)

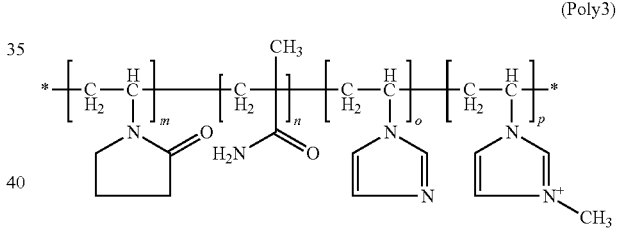

(Poly3)

wherein indices m, n, o and p vary according to the molecular mass of the polymer and are not intended to mean to portray block copolymers. In fact, structural units of Formula (M11-a), (M6), (M8) and (M12) can be statistically distributed in the molecule.

To compensate for the positive polymer charge of the component (c3), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate the positive charge of the polymer of Formula (Poly3), then these N-methyl vinylimidazole/vinyl pyrrolidone/vinyl imidazole/methacrylamide copolymers are named according to INCI nomenclature as Polyquaternium-68 and are available from, for example, BASF under the trade name Luviquat® Supreme.

Quite particularly preferred copolymers (c3) have 1 to 12 mol %, preferably 3 to 9 mol % and particularly 6 mol % of structural units according to Formula (M11-a), 45 to 65 mol %, preferably 50 to 60 mol % and particularly 55 mol % of structural units according to Formula (M6), 1 to 20 mol %, preferably 5 to 15 mol % and particularly 10 mol % of structural units according to Formula (M8), and 20 to 40 mol %, preferably 25 to 35 mol % and particularly 29 mol % of structural units according to Formula (M12).

Particularly preferred agents include a copolymer (c3) having molecular masses within a defined range. Here, agents are preferred wherein the molecular mass of copolymer (c3) is from 100 to 500 kDa, preferably from 150 to 400 kDa, more preferably from 250 to 350 kDa and particularly from 290 to 310 kDa.

Preferred additional film-forming cationic and/or setting polymers, chosen from cationic polymers having at least one structural element of the above Formula (M11-a), include:

- vinyl pyrrolidone/1-vinyl-3-methyl-1H-imidazolium chloride copolymers (such as that with the INCI name Polyquaternium-16 sold under the trade names Luviquat® Style, Luviquat® FC 370, Luviquat® FC 550, Luviquat® FC 905 and Luviquat® HM 552 (BASF SE)),
- vinyl pyrrolidone/1-vinyl-3-methyl-1H-imidazolium methyl sulfate copolymers (such as that with the INCI name Polyquaternium-44 sold under the trade name Luviquat® Care (BASF SE)),
- vinyl pyrrolidone/vinyl caprolactam/1-vinyl-3-methyl-1H-imidazolium terpolymer (such as that with the INCI name Polyquaternium-46 sold under the trade names Luviquat® Care or Luviquat® Hold (BASF SE)), and
- vinyl pyrrolidone/methacrylamide/vinyl imidazole/1-vinyl-3-methyl-1H-imidazolium methyl sulfate copolymer (such as that with the INCI name Polyquaternium-68 sold under the trade name Luviquat® Supreme (BASF SE)), as well as mixtures of these polymers.

Further preferred cationic polymers that can be used in the inventive agents are the "temporarily cationic" polymers. These polymers usually have an amino group that is present at specific pH values as a quaternary ammonium group and is thus cationic.

These polymers include chitosan, for example. According to the present invention, chitosan and/or chitosan derivatives are considered as quite particularly preferred suitable film-forming and/or setting polymers.

Chitosans are biopolymers and are considered to be a hydrocolloid. From the chemical point of view, they are partially deacetylated chitins of different molecular weight.

Chitosan is manufactured from chitin, preferably from the remains of crustacean shells, which are available in large quantities as a cheap raw material. For this, the chitin is firstly deproteinated by adding bases, demineralized by adding mineral acids and finally deacetylated by adding strong bases, wherein the molecular weights can vary over a wide spectrum. Those types are preferably used that have an average molecular weight of 800,000 to 1,200,000 Dalton, a Brookfield viscosity (1 wt. % conc. in glycolic acid) of 5000 mPas or less, a deacetylation degree in the range 80 to 88%, and an ash content of 0.3 wt. % or less.

According to the invention, besides chitosans as the typical cationic biopolymers, cationically derivatized chitosans can also be considered (such as quaternized products) or alkoxylated chitosans.

Preferred agents contain neutralization products of chitosan neutralized with at least one acid chosen from lactic acid, pyrrolidone carboxylic acid, nicotinic acid, hydroxy-iso-butyric acid, or hydroxy-iso-valeric acid, or contain mixtures of these neutralization products as the chitosan derivative(s).

Exemplary suitable chitosan (derivatives) are freely available on the market under the trade names Hydagen® CMF (1 wt. % active substance in aqueous solution with 0.4 wt. % glycolic acid, molecular weight 500,000 to 5,000,000 g/mol Cognis), Hydagen® HCMF (chitosan (80% deacetylated), molecular weight 50,000 to 1 000 000 g/mol, Cognis), Kytamer® PC (80 wt. % active substance of chitosan pyrrolidone carboxylate (INCI name: Chitosan PCA), Amerchol) and Chitolam® NB/101.

Agents according to the invention preferably include chitosan or its derivatives in an amount of 0.01 wt. % to 20.0 wt. %, particularly preferably 0.01 wt. % to 10.0 wt. %, quite particularly preferably 0.1 wt. % to 1 wt. %, based on total weight of the agent.

According to the invention, preferred temporarily cationic polymers are likewise those having at least one structural unit of Formulas (M1-1) to (M1-8)

(M1-1)

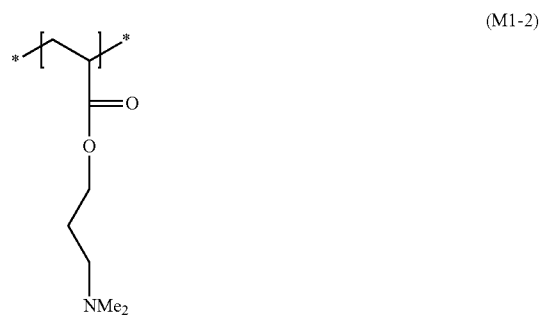

(M1-2)

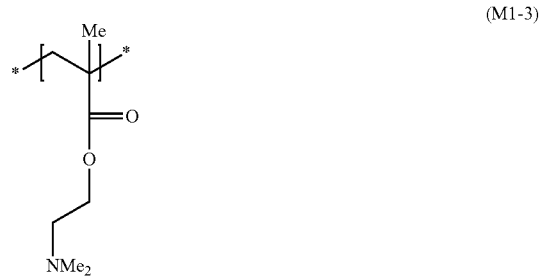

(M1-3)

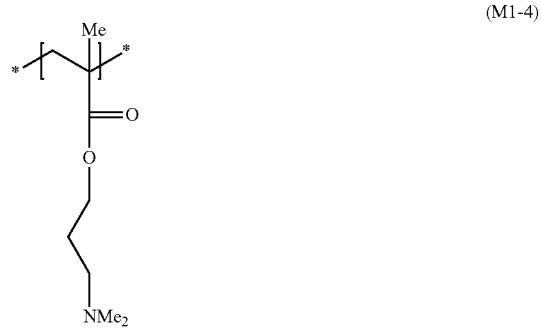

(M1-4)

-continued (M1-5)
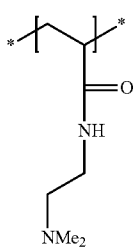

(M1-6)
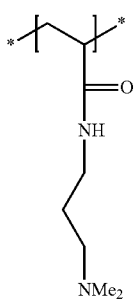

(M1-7)
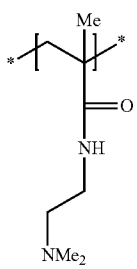

(M1-8)
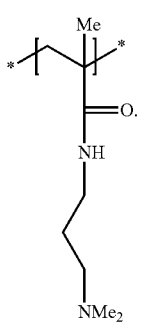

In this regard, those copolymers are again preferred that have at least one structural unit of Formulas (M1-1) to (M1-8) and additionally at least one structural unit of Formula (M10), (M10)
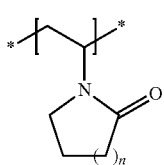

wherein n is 1 or 3.

Here again, the group of polymers
N-vinyl pyrrolidone/N-vinyl caprolactam/dimethylaminopropylmethacrylamide copolymer (for example INCI name: VP/Vinyl Caprolactam/DMAPA Acrylates Copolymer under the trade name Aquaflex® SF-40 (ISP)), N-vinyl caprolactam/N-vinyl pyrrolidone/dimethylaminoethyl methacrylate copolymer (for example as 35-39% solids in ethanol in the form of the commercial product Advantage LC E with the INCI name: Vinyl Caprolactam/VP/Dimethylaminoethyl Methacrylate Copolymer, Alcohol, Lauryl Pyrrolidone (ISP)), N-vinyl pyrrolidone/dimethylaminopropylmethacrylamide copolymer (for example INCI name: VP/DMAPA Acrylates Copolymer under the trade name Styleze® CC-10 (ISP)), forms the preferred list for selection.

Agents according to the invention can also have at least one amphoteric polymer as the film-forming and/or setting polymer. The term amphoteric polymers includes not only those polymers whose molecule has both free amino groups and free —COOH or $SO_3H$ groups and which are capable of forming inner salts, but also zwitterionic polymers whose molecule has quaternary ammonium groups and —COO⁻ or —$SO_3^-$ groups, and those polymers having —COOH or $SO_3H$ groups and quaternary ammonium groups.

An example of a useful amphopolymer according to the invention is the acrylic resin obtainable under the designation Amphomer®, which is a copolymer of tert-butylaminoethyl methacrylate, N-(1,1,3,3-tetramethylbutyl)acrylamide, and two or more monomers from the group consisting of acrylic acid, methacrylic acid and their simple esters.

The latter, in addition to the cationogenic group or the positively charged group, have at least one negatively charged group in the molecule and are also called zwitterionic polymers.

Agents according to the invention preferably have amphoteric polymers in amounts of 0.01 to 20 wt. %, particularly preferably 0.05 to 10 wt. %, based on total weight of the agent. Quantities of 0.1 to 5% by weight are particularly preferred.

Furthermore, at least one anionic film-forming and/or anionic setting polymer can be used as the film-forming and/or setting polymers.

Anionic polymers concern anionic polymers having carboxylate and/or sulfonate groups. Exemplary anionic monomers from which such polymers can be made are acrylic acid, methacrylic acid, crotonic acid, maleic anhydride and 2-acrylamido-2-methylpropane sulfonic acid. Here, the acidic groups may be fully or partially present as sodium, potassium, ammonium, mono- or triethanolammonium salts.

Within this embodiment, it can be preferred to use copolymers of at least one anionic monomer and at least one non-ionic monomer. Regarding the anionic monomers, reference is made to the abovementioned substances. Preferred non-ionic monomers are acrylamide, methacrylamide, acrylic acid esters, methacrylic acid esters, vinyl pyrrolidone, vinyl ethers and vinyl esters.

Preferred anionic copolymers are acrylic acid-acrylamide copolymers, particularly polyacrylamide copolymers with monomers containing sulfonic acid groups. A particularly preferred anionic copolymer contains 70 to 55 mole % acrylamide and 30 to 45 mole % 2-acrylamido-2-methylpropane sulfonic acid, wherein the sulfonic acid group may be fully or partially present as the sodium, potassium, ammonium, mono- or triethanolammonium salt. This copolymer can also be crosslinked, wherein the preferred crosslinking agents include polyolefinically unsaturated compounds such as tetraallyloxyethane, allyl sucrose, allyl pentaerythritol and methylene bisacrylamide. Such a polymer is present in the commercial product Sepigel® 305 from the SEPPIC Company. Use of this compound, which has a mixture of hydrocarbons ($C_{13}$-$C_{14}$ isoparaffins) and a non-ionic emulsifier (Laureth-7) in addition to the polymer components, has proved to be particularly advantageous.

Sodium acryloyl dimethyl taurate copolymers commercially available as a compound with isohexadecane and polysorbate 80 under the trade name Simulgel® 600 have also proved to be particularly effective according to the invention.

Likewise preferred anionic homopolymers are uncrosslinked and crosslinked polyacrylic acids. Here, preferred crosslinking agents can be allyl ethers of pentaerythritol, sucrose and propylene. Such compounds are commercially available, for example, under the trade name Carbopol®.

Further preferred employable anionic polymers are chosen from:
- copolymers of vinyl acetate and crotonic acid (as marketed, for example, as the commercial product Aristoflex® A 60 with the INCI name VA/Crotonates Copolymer by CIBA in a 60 wt. % conc. dispersion in isopropanol-water),
- copolymers of ethyl acrylate and methacrylic acid (as marketed, for example, under the trade name Luviflex® Soft with an acid number of 84 to 105 under the INCI name Acrylates Copolymer in a ca. 20 to 30 wt. % conc. dispersion in water by BASF SE),
- Polyurethanes containing at least one carboxyl group (such as a copolymer of isophthalic acid, adipic acid, 1,6-hexane diol, neopentyl glycol and isophorone diisocyanate as marketed under the trade name Luviset® PUR with the INCI name Polyurethane-1 by BASF SE).

When particularly strong acting thickening anionic polymers are used, then according to a preferred embodiment, care should be taken that the previously cited preferred viscosity criterion of agents according to the invention is adhered to.

Copolymers of maleic anhydride and methyl vinyl ether, especially those with crosslinks, are also color-conserving polymers. A maleic acid-methyl vinyl ether copolymer crosslinked with 1,9-decadiene is commercially available under the name Stabileze® QM.

In order to intensify the effect according to the invention, the agents preferably additionally contain at least one surfactant, with non-ionic, anionic, cationic, ampholytic surfactants being suitable. The group of ampholytic or also amphoteric surfactants includes zwitterionic surfactants and ampholytes. According to the invention, the surfactants can already have an emulsifying action.

The agent preferably contains surfactants in an amount of 0.01 wt. % to 5 wt. %, particularly preferably 0.05 wt. % to 0.5 wt. %, based on total weight of the agent.

It has proved particularly preferable when the agents have at least one non-ionic surfactant.

Non-ionic surfactants can include a polyol group, a polyalkylene glycol ether group or a combination of polyol ether groups and polyglycol ether groups as the hydrophilic group. Exemplary compounds of this type are
- addition products of 2 to 100 moles ethylene oxide and/or 1 to 5 moles propylene oxide to linear and branched fatty alcohols containing 8 to 30 carbon atoms, to fatty acids containing 8 to 30 carbon atoms, and to alkyl phenols containing 8 to 15 carbon atoms in the alkyl group,
- methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms, and to alkyl phenols with 8 to 15 carbon atoms in the alkyl group, such as the commercially available types Dehydrol® LS, Dehydrol® LT (Cognis),
- $C_{12}$-$C_{30}$ fatty acid mono- and diesters of addition products of 1 to 30 moles ethylene oxide to glycerin,
- addition products of 5 to 60 moles ethylene oxide on castor oil and hydrogenated castor oil,
- polyol esters of fatty acids, such as the commercial product Hydagen® HSP (Cognis) or Sovermol types (Cognis),
- alkoxylated triglycerides,
- alkoxylated alkyl esters of fatty acids of Formula (E4-I),

$$R^1CO\text{—}(OCH_2CHR^2)_wOR^3 \quad \text{(E4-I)}$$

wherein $R^1CO$ is a linear or branched, saturated and/or unsaturated acyl group with 6 to 22 carbon atoms, $R^2$ is hydrogen or methyl, $R^3$ is linear or branched alkyl groups with 1 to 4 carbon atoms and w is a number from 1 to 20,
- amine oxides,
- mixed hydroxy ethers, such as are described in DE-OS 1 973 8866,
- sorbitol esters of fatty acids and addition products of ethylene oxide to sorbitol esters of fatty acids such as polysorbates,
- sugar esters of fatty acids and addition products of ethylene oxide to sugar esters of fatty acids,
- addition products of ethylene oxide to fatty acid alkanolamides and fatty amines,
- sugar surfactants of the type alkyl and alkenyl oligoglycosides according to Formula (E4-II),

$$R^4O[G]_p \quad \text{(E4-II)}$$

wherein $R^4$ is an alkyl or alkenyl group containing 4 to 22 carbon atoms, G is a sugar group containing 5 or 6 carbon atoms, and p is a number from 1 to 10. They can be obtained according to the appropriate methods of preparative organic chemistry.

Alkylene oxide addition products to saturated, linear fatty alcohols and fatty acids, each having 2 to 100 moles ethylene oxide per mole fatty alcohol or fatty acid, have proved to be quite particularly preferred non-ionic surfactants. Similarly, preparations with excellent properties are obtained when they have $C_{12}$-$C_{30}$ fatty acid mono- and diesters of addition products of 1 to 30 moles ethylene oxide to glycerin and/or addition products of 5 to 60 moles ethylene oxide to castor oil and hydrogenated castor oil as the non-ionic surfactants.

Agents according to the invention quite particularly preferably have as the surfactant at least one addition product of 15 to 100 moles ethylene oxide, especially 15 to 50 moles ethylene oxide on a linear or branched (especially linear) fatty alcohol containing 8 to 22 carbon atoms. These are quite preferably Ceteareth-15, Ceteareth-25 or Ceteareth-50, marketed as Eumulgin® CS 15 (COGNIS), Cremophor A25 (BASF SE) or Eumulgin® CS 50 (COGNIS).

Suitable anionic surfactants include all anionic surface-active materials suitable for use on the human body. They have a water solubilizing anionic group such as a carboxylate, sulfate, sulfonate or phosphate group and a lipophilic alkyl group containing about 8 to 30 carbon atoms. In addition, the molecule may have glycol or polyglycol ether groups, ester, ether and amide groups, as well as hydroxyl groups. Exemplary suitable anionic surfactants are, each in the form of the sodium, potassium and ammonium as well as the mono, di and trialkanolammonium salts containing 2 to 4 carbon atoms in the alkanol group,
- linear and branched fatty acids having 8 to 30 carbon atoms (soaps),
- ether carboxylic acids of the Formula R—O—($CH_2$—$CH_2O)_x$—$CH_2$—COOH, wherein R is a linear alkyl group having 8 to 30 carbon atoms and x=0 or 1 to 16, acyl sarcosides having 8 to 24 carbon atoms in the acyl group,
acyl taurides having 8 to 24 carbon atoms in the acyl group,
acyl isethionates having 8 to 24 carbon atoms in the acyl group,
mono- and dialkyl esters of sulfosuccinic acid having 8 to 24 carbon atoms in the alkyl group and mono-alkyl polyoxyethyl esters of sulfosuccinic acid having 8 to 24 carbon atoms in the alkyl group and 1 to 6 oxyethylene groups,
linear alkane sulfonates having 8 to 24 carbon atoms,
linear alpha-olefin sulfonates having 8 to 24 carbon atoms,
alpha-sulfo fatty acid methyl esters of fatty acids having 8 to 30 carbon atoms,
alkyl sulfates and alkyl polyglycol ether sulfates of the Formula R—O(CH$_2$—CH$_2$O)$_x$—OSO$_3$H, wherein R is preferably a linear alkyl group having 8 to 30 carbon atoms and x=0 or 1 to 12,
mixtures of surface-active hydroxysulfonates,
sulfated hydroxyalkyl polyethylene glycol ethers and/or hydroxyalkylene propylene glycol ethers,
sulfonates of unsaturated fatty acids having 8 to 24 carbon atoms and 1 to 6 double bonds,
esters of tartaric acid and citric acid with alcohols, which represent the addition products of about 2-15 molecules of ethylene oxide and/or propylene oxide on fatty alcohols having 8 to 22 carbon atoms,
sulfated fatty acid alkylene glycol esters of Formula (E1-II)

$$R^7CO(AlkO)_nSO_3M \quad (E1\text{-}II)$$

wherein R$^7$CO— is a linear or branched, aliphatic, saturated and/or unsaturated acyl group having 6 to 22 carbon atoms, Alk is CH$_2$CH$_2$, CHCH$_3$CH$_2$ and/or CH$_2$CHCH$_3$, n is a number from 0.5 to 5, and M is a cation, as described in DE-OS 197 36 906,
amido ether carboxylic acids, and
condensation products of C$_8$-C$_{30}$ fatty alcohols with protein hydrolyzates and/or amino acids and their derivatives, known to one skilled in the art as albumin fatty acid condensates, such as the Lamepon® types, Gluadin® types, Hostapon® KCG or the Amisoft® types.

Preferred anionic surfactants are alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerin disulfates, alkyl- and alkenyl ether phosphates as well as albumin fatty acid condensates.

According to the invention, cationic surfactants of the type quaternary ammonium compounds, esterquats and amido amines can likewise be used. Preferred quaternary ammonium compounds are ammonium halides, especially chlorides and bromides, such as alkyl-trimethyl ammonium chlorides, dialkyldimethylammonium chlorides and trialkylmethylammonium chlorides. The long alkyl chains of these surfactants preferably have 10 to 18 carbon atoms, such as in cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further preferred cationic surfactants are those imidazolium compounds known under the INCI names Quaternium-27 and Quaternium-83.

Zwitterionic surfactants are those surface-active compounds having at least one quaternary ammonium group and at least one —COO$^{(-)}$ or —SO$_3^{(-)}$ group in the molecule. Particularly preferred suitable zwitterionic surfactants are betaines such as N-alkyl-N,N-dimethylammonium glycinates, for example, the cocoalkyl-dimethylammonium glycinate, N-acyl-aminopropyl-N,N-dimethylammonium glycinate, for example, the coco-acylaminopropyl-dimethylammonium glycinate, and 2-alkyl-3-carboxymethyl-3-hydroxyethyl-imidazolines, each with 8 to 18 carbon atoms in the alkyl or acyl group as well as the cocoacyl-aminoethylhydroxyethylcarboxymethyl glycinate. A preferred zwitterionic surfactant is the fatty acid amide derivative known under the INCI name Cocamidopropyl Betaine.

Ampholytes include such surface-active compounds that, apart from a C$_{8-24}$ alkyl or acyl group, have at least one free amino group and at least one —COOH or —SO$_3$H group in the molecule and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycines, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and C$_{12}$-C$_{18}$ acyl sarcosine.

Agents according to the invention contain the ingredients or active substances in a cosmetically acceptable carrier.

Preferred cosmetically acceptable carriers are aqueous, alcoholic or aqueous alcoholic media containing preferably at least 10 wt. % water, based on total weight of the composition. In particular, lower alcohols having 1 to 4 carbon atoms, such as ethanol and isopropanol, which are usually used for cosmetic purposes, can be used as alcohols. Preferably, at least one (C$_1$ to C$_4$) monoalkyl alcohol is incorporated into the agents, particularly in an amount of 1 to 50 wt. %, especially 5 to 30 wt. %. Again, this is particularly preferred when manufacturing pump foams or aerosol foams.

Organic solvents or mixture of solvents with a boiling point of less than 400° C. can be present as additional co-solvents in an amount of 0.1 to 15 wt. %, preferably 1 to 10 wt. %, based on total weight of the agent. Particularly suitable additional co-solvents are unbranched or branched hydrocarbons such as pentane, hexane, isopentane and cyclic hydrocarbons such as cyclopentane and cyclohexane. Additional, particularly preferred water-soluble solvents are glycerin, ethylene glycol and propylene glycol in an amount of up to 30 wt. %, based on total weight of the agent.

The addition of glycerin and/or propylene glycol and/or polyethylene glycol and/or polypropylene glycol in particular increases the flexibility of the polymer film formed when the agent is used. Consequently, if a more flexible hold is desired, then agents according to the invention preferably comprise 0.01 to 30 wt. % glycerin and/or propylene glycol and/or polyethylene glycol and/or polypropylene glycol, based on total weight of the agent.

The agents preferably have a pH of 2 to 11. The pH range is particularly preferably from 2 to 8. In the context of this publication, pH data refers to pH at 25° C. unless otherwise stated.

Agents according to the invention can additionally include auxiliaries and additives that are usually incorporated into conventional styling agents.

In particular, care products may be mentioned as suitable auxiliaries and additives.

Silicone oil and/or a silicone gum, for example, can be employed as the care substance.

Suitable silicone oils or silicone gums according to the invention include dialkyl and alkylarylsiloxanes such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils provide a variety of effects. Thus, for example, they simultaneously influence the dry and wet combability, the feel of the dry and wet hair as well as the gloss. The term "silicone oils" is understood by one skilled in the art to mean organosilicon compounds with a plurality of structures. In the first instance they include the Dimethiconols. The following commercial products are given as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel S1 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), San-Surf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), THV 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones form the second group of silicones that can be used according to the invention. They can be linear, branched, cyclic, or cyclic and branched.

Dimethicone copolyols form a further group of suitable silicones. Suitable Dimethicone copolyols are commercially available and marketed, for example, by Dow Corning under the trade name Dow Corning® 5330 Fluid.

Naturally, the Dimethiconols, Dimethicones and/or Dimethicone copolymers can already be present as an emulsion. The corresponding emulsions of the Dimethiconols, Dimethicones and/or Dimethicone copolyols can be produced both after production of the corresponding Dimethiconols, Dimethicones and/or Dimethicone copolyols from these and the usual emulsification processes known to one skilled in the art. Cationic, anionic, non-ionic or zwitterionic surfactants and emulsifiers can be used as auxiliaries and adjuvants for production of the corresponding emulsions. Naturally, emulsions of the Dimethiconols, Dimethicones and/or Dimethicone copolyols can also be produced directly by an emulsion polymerization process. These types of processes are also well known to one skilled in the art.

When Dimethiconols, Dimethicones and/or Dimethicone copolyols are used as an emulsion, then droplet size of the emulsified particles ranges from 0.01 to 10,000 µm, preferably 0.01 to 100 µm, particularly preferably 0.01 to 20 µm and quite particularly preferably 0.01 to 10 µm. Particle size is determined according to the light scattering method.

If branched Dimethiconols, Dimethicones and/or Dimethicone copolyols are used, then it is understood that the branching is greater than a fortuitous branching that accidentally results from impurities in the respective monomers. Accordingly, in the context of the present invention, the degree of branching is understood to be 0.01% or greater for branched Dimethiconols, Dimethicones and/or Dimethicone copolyols. The degree of branching is preferably 0.01% or greater and quite particularly preferably 0.5% or greater. The degree of branching is determined from the ratio of unbranched monomers to branched monomers (i.e., the amount of tri- and tetrafunctional siloxanes). According to the invention, both low-branched and highly branched Dimethiconols, Dimethicones and/or Dimethicone copolyols can be quite particularly preferred.

Further suitable silicones are amino-functional silicones, especially those silicones compiled under the INCI name Amodimethicone. Consequently, it is inventively preferred when the agents additionally have at least one amino-functional silicone. These refer to silicones having at least one, optionally substituted, amino group. These silicones are designated as Amodimethicones according to INCI nomenclature and are available, for example, in the form of an emulsion as the commercial product Dow Corning® 939 or as the commercial product Dow Corning® 949 in a mixture with a cationic and a non-ionic surfactant.

Preferably, those amino functional silicones are used which have an amine number of 0.25 meq/g or greater, preferably 0.3 meq/g or greater, and particularly preferably 0.4 meq/g or greater. The amine number is the milli-equivalents of amine per gram of amino functional silicone. It can be measured by titration and can also be reported with the unit mg KOH/g.

The agents preferably include silicones in amounts of 0.01 wt. % to 15 wt. %, particularly preferably in amounts of 0.05 to 2 wt. %, based on total weight of the agent.

The composition can include, for example, at least one protein hydrolyzate and/or one of its derivatives as a care substance of another compound class.

Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. The molecular weight of protein hydrolyzates utilizable according to the invention ranges from 75, the molecular weight of glycine, to 200,000, preferably the molecular weight is 75 to 50,000 and quite particularly preferably 75 to 20,000 Dalton.

According to the invention, the added protein hydrolyzates can be vegetal as well as animal or marine or synthetic origin.

Animal protein hydrolyzates include elastin, collagen, keratin, silk protein, and milk albumin protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

Agents according to the invention contain protein hydrolyzates, for example, in concentrations of 0.01 wt. % to 20 wt.

%, preferably 0.05 wt. % up to 15 wt. % and quite particularly preferably in amounts of 0.05 wt. % up to 5 wt. %, based on total weight of the end-use preparation.

The agent can further have at least one vitamin, one provitamin, one vitamin precursor and/or one of their derivatives as the care substance.

According to the invention, such vitamins, provitamins and vitamin precursors are preferred, which are normally classified in the groups A, B, C, E, F and H.

Substances designated as vitamin A includes retinol (vitamin $A_1$) as well as 3,4-didehydroretinol (vitamin $A_2$). β-Carotene is the provitamin of retinol. Examples of suitable vitamin A components are vitamin A acid and its esters, vitamin A aldehyde and vitamin A alcohol as well as its esters such as the palmitate and acetate. The agents preferably contain vitamin A components in amounts of 0.05 to 1 wt. %, based on total weight of the application preparation.

The vitamin B group or the vitamin B complex include inter alia vitamin $B_1$ (thiamine), vitamin $B_2$ (riboflavin), vitamin $B_3$ (nicotinic acid and/or nicotinic acid amide (niacinamide)), vitamin $B_5$ (pantothenic acid, panthenol and pantolactone), vitamin $B_6$ (pyridoxine as well as pyridoxamine and pyridoxal), vitamin C (ascorbic acid), vitamin E (tocopherols, especially α-tocopherol), vitamin F (linoleic acid and/or linolenic acid), vitamin H.

The agents preferably contain vitamins, provitamins and vitamin precursors from groups A, B, C, E and H. Panthenol, pantolactone, pyridoxine and its derivatives as well as nicotinamide and biotin are especially preferred.

D-panthenol is quite particularly preferably employed as a care substance, optionally in combination with at least one of the abovementioned silicone derivatives.

Like the addition of glycerin and/or propylene glycol, the addition of panthenol increases the flexibility of the polymer film formed when the agent is used. Thus, if a particularly flexible hold is desired, then the agents can include panthenol instead of or in addition to glycerin and/or propylene glycol. In a preferred embodiment, the agents contain panthenol, preferably in a quantity of 0.05 to 10 wt. %, particularly preferably 0.1 to 5 wt. %, based on total weight of the agent.

The agents can further include at least one plant extract as a care substance.

Usually, these extracts are manufactured by extraction of the whole plant. In individual cases, however, it can also be preferred to produce the extracts solely from blossoms and/or leaves of the plant.

According to the invention, mainly extracts from green tea, oak bark, stinging nettle, hamamelis, hops, henna, chamomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, restharrow, coltsfoot, marshmallow (althaea), meristem, ginseng and ginger are preferred.

In addition, it can be preferred to use mixtures of a plurality, particularly two different plant extracts, in the agents.

Mono- or oligosaccharides can also be incorporated as care substance into agents according to the invention.

Both monosaccharides as well as oligosaccharides such as raw sugar, lactose and raffinose can be incorporated. According to the invention, use of monosaccharides is preferred. Once again, monosaccharides preferably include those compounds having 5 or 6 carbon atoms.

Suitable pentoses and hexoses include ribose, arabinose, xylose, lyxose, allose, altrose, glucose, mannose, gulose, idose, galactose, talose, fucose and fructose.

Arabinose, glucose, galactose and fructose are the preferred incorporated carbohydrates; glucose is quite particularly preferably incorporated, and is suitable both in the D(+) or L(−) configuration or as the racemate.

In addition, derivatives of these pentoses and hexoses can also be incorporated according to the invention, such as the corresponding onic and uronic acids (sugar acids), sugar alcohols, and glycosides.

Preferred sugar acids are the gluconic acid, the glucuronic acid, the sugar acids, the mannosugar acids and the mucic acids. Preferred sugar alcohols are sorbitol, mannitol and dulcitol.

Preferred glycosides are methyl glucosides.

As the incorporated mono- and oligosaccharides are usually obtained from natural raw materials such as starch, they generally possess the configurations that correspond to these raw materials (e.g. D-glucose, D-fructose and D-galactose).

The agents preferably contain mono- or oligosaccharides in an amount of 0.1 to 8 wt. %, particularly preferably 1 to 5 wt. %, based on total weight of the end-use preparation.

The agent can further have at least one lipid as a care substance.

According to the invention, suitable lipids are phospholipids, for example, soy lecithin, egg lecithin and cephalins, as well as the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PTC® and Phospholipid SV®. The agents preferably have lipids in amounts of 0.01 to 10 wt. %, in particular 0.1 to 5 wt. %, based on total weight of the end-use preparation.

Oil bodies are also suitable as a care substance.

Natural and synthetic cosmetic oil bodies include:

vegetal oils. Examples of such oils are sunflower oil, olive oil, soya oil, rapeseed oil, almond oil, jojoba oil, orange oil, wheat germ oil, peach stone oil and the liquid parts of coconut oil. Other triglyceride oils such as the liquid fractions of beef tallow as well as synthetic triglyceride oils are also suitable, however.

liquid paraffin oils, isoparaffin oils and synthetic hydrocarbons as well as di-n-alkyl ethers containing a total of 12 to 36 carbon atoms, particularly 12 to 24 carbon atoms such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. Commercial products of the compounds 1,3-di-(2-ethylhexyl)cyclohexane (Cetiol® S) and di-n-octyl ether (Cetiol® OE) can be preferred.

Ester oils. Ester oils refer to esters of $C_6$-$C_{30}$ fatty acids with $C_2$-$C_{30}$ fatty alcohols. Monoesters of fatty acids with alcohols containing 2 to 24 carbon atoms are preferred. According to the invention, isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerin tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butane diol di-isostearate, neopentyl glycol dicaprylate, symmetrical, unsymmetrical or cyclic esters of carbon dioxide with fatty alcohols, for example, as described in DE-OS 197 56 454, glycerine carbonate or dicaprylyl carbonate (Cetiol® CC), trifatty acid esters of saturated and/or unsaturated linear and/or branched fatty acids with glycerin, fatty acid partial glycerides, under which are understood monoglycerides, diglycerides and their industrial mixtures. When using industrial products, minor amounts of triglycerides may still be contained as a result of the production process. The partial glycerides preferably comply with the Formula (D4-I),

wherein $R^1$, $R^2$ and $R^3$ are, independently of each other, hydrogen or a linear or branched, saturated and/or unsaturated acyl group containing 6 to 22 carbon atoms, preferably 12 to 18 carbon atoms, with the proviso that at least one of these groups is an acyl group and at least one of these groups is hydrogen. The sum of (m+n+q) is 0 or a number from 1 to 100, preferably 0 or 5 to 25. Preferably, $R^1$ is an acyl group, $R^2$ and $R^3$ are hydrogen, and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The added amount of natural and synthetic cosmetic oil bodies in agents according to the invention is usually 0.1 to 30 wt. %, based on total weight of the end-use preparation, preferably 0.1 to 20 wt. % and particularly 0.1 to 15 wt. %.

Although each of the cited care substances alone already provides a satisfactory result, in the context of the present invention all embodiments are included wherein the agent contains a plurality of conditioners, even from different groups.

By addition of a UV filter, both the agent and the treated fibers can be protected against damage from UV radiation. Consequently, at least one UV filter is preferably added to the agent. Suitable UV filters are not generally limited in regard to their structure and their physical properties. Indeed, all UV filters that can be employed in the cosmetic field having an absorption maximum in the UVA (315-400 nm), UVB (280-315 nm) or UVC (<280 nm) regions are suitable. UV filters having an absorption maximum in the UVB region, especially in the range from about 280 to about 300 nm, are particularly preferred.

Preferred UV-filters are chosen from substituted benzophenones, p-aminobenzoates, diphenylacrylates, cinnamates, salicylates, benzimidazoles and o-aminobenzoates.

Exemplary usable UV-filters are 4-amino-benzoic acid, N,N,N-trimethyl-4-(2-oxoborn-3-ylidenemethyl)aniline methylsulfate, 3,3,5-trimethylcyclohexyl salicylate (Homosalate), 2-hydroxy-4-methoxy-benzophenone (Benzophenone-3; Uvinul® M 40, Uvasorb® MET, Neo Heliopan® BB, Eusolex® 4360), 2-phenylbenzimidazol-5-sulfonic acid and their potassium, sodium and triethanolamine salts (phenylbenzimidazole sulfonic acid; Parsol® HS; Neo Heliopan® Hydro), 3,3'-(1,4-phenylenedimethylene)-bis(7,7-dimethyl-2-oxo-bicyclo-[2.2.1]hept-1-yl-methanesulfonic acid) and their salts, 1-(4-tert.-butylphenyl)-3-(4-methoxyphenyl) propane-1,3-dione (butylmethoxydibenzoylmethane; Parsol® 1789, Eusolex® 9020), a-(2-oxoborn-3-ylidene)-toluene-4-sulfonic acid and salts thereof, ethoxylated ethyl 4-aminobenzoate (PEG-25 PABA; Uvinul® P 25), 2-ethylhexyl 4-dimethylaminobenzoate (Octyl Dimethyl PABA; Uvasorb® DMO, Escalol® 507, Eusolex® 6007), 2-ethylhexyl salicylate (Octyl Salicylate; Escalol® 587, Neo Heliopan® OS, Uvinul® 018), isopentyl 4-methoxycinnamate (isoamyl p-methoxycinnamate; Neo Heliopan® E 1000), 2-ethylhexyl 4-methoxycinnamate (Octyl Methoxycinnamate; Parsol® MCX, Escalol® 557, Neo Heliopan® AV), 2-hydroxy-4-methoxybenzophenone-5-sulfonic acid and sodium salts thereof, (benzophenone-4; Uvinul® MS 40; Uvasorb® S 5), 3-(4'-methylbenzylidene)-D,L-camphor (4-methylbenzylidene camphor; Parsol® 5000, Eusolex® 6300), 3-benzylidene-camphor (3-Benzylidene camphor), 4-isopropylbenzyl salicylate, 2,4,6-trianilino-(p-carbo-2'-ethylhexyl-1'-oxy)-1,3,5-triazine, 3-imidazol-4-yl-acrylic acid and its ethyl ester, polymers of N-{(2 and 4)-[2-oxoborn-3-ylidenemethyl]benzyl}-acrylamide, 2,4-dihydroxybenzophenone (Benzophenone-1; Uvasorb® 20 H, Uvinul® 400), 2-ethylhexyl ester of 1,1'-diphenylacrylonitrilic acid (Octocrylene; Eusolex® OCR, Neo Heliopan® Type 303, Uvinul® N 539 SG), menthyl o-aminobenzoate (menthyl anthranilate; Neo Heliopan® MA), 2,2',4,4'-tetrahydroxybenzophenone (Benzophenone-2, Uvinul® D-50), 2,2'-dihydroxy-4,4'-dimethoxybenzophenone (Benzophenone-6), sodium 2,2'-dihydroxy-4,4'-dimethoxybenzophenone-5-sulfonate and 2'-ethylhexyl 2-cyano-3,3-diphenylacrylate. 2-Hydroxy-4-methoxy-benzophenone-5-sulfonic acid and its sodium salt and/or ethoxylated ethyl 4-aminobenzoate are preferred.

The agent usually contains UV filters in amounts of 0.01 to 5 wt. %, based on total weight of the end-use preparation. Quantities of 0.1-2.5 wt. % are preferred.

In a particular embodiment, the agent further contains one or more substantive dyes. Application of the agent then enables the treated keratinic fiber not only to be temporarily styled but also to be dyed at the same time. This can be particularly desirable when only a temporary dyeing is desired, for example with flamboyant fashion colors that can be subsequently removed from the keratinic fibers by simply washing them out.

Substantive dyes are usually nitrophenylenediamines, nitroamino phenols, azo dyes, anthraquinones or indophenols. Preferred substantive dyestuffs are those under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, TIC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 known compounds as well as 1,4-diamino-2-nitrobenzene, 2-amino-4-nitrophenol, 1,4-bis(β-hydroxyethypamino-2-nitrobenzene, 3-nitro-4(β-hydroxyethyl)aminophenol, 2-(2'-hydroxyethyl)amino-4-6-dinitrophenol, 1-(2'-hydroxyethyl) amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene. Cationic substantive dyes are preferably employed. Particular preference is given here to (a) cationic triphenylmethane dyes, such as Basic Blue 7, Basic Blue 26, Basic Violet 2 and Basic Violet 14,
(b) aromatic systems substituted by a quaternary nitrogen group, such as Basic Yellow 57, Basic Red 76, Basic Blue 99, Basic Brown 16 and Basic Brown 17, and
(c) substantive dyes having a heterocycle that has at least one quaternary nitrogen atom, as specified, for example, in EP-A2-998 908 in claims 6 to 11.

Dyes also known under the names Basic Yellow 87, Basic Orange 31 and Basic Red 51 are quite particularly preferred cationic substantive dyes of group (c). Cationic substantive dyes commercialized under the trade name Arianor® are likewise quite particularly preferred cationic substantive dyes according to the invention.

Agents according to this embodiment contain substantive dyes preferably in an amount of 0.001 to 20 wt. %, based on total weight of the agent.

Preferably, the agents are exempt from oxidation dye precursors. Oxidation dye precursors are divided into developer components and coupler components. Under the influence of oxidizing agents or atmospheric oxygen, developer components form the actual colorants among each other or by coupling with one or more coupler components.

Formulation of the agents can be in all usual forms for styling agents, for example, in the form of solutions that can be applied as hair water or pump or aerosol spray onto the hair, in the form of creams, emulsions, waxes, gels or also surfactant-containing foaming solutions or other preparations suitable for application on the hair.

In another embodiment, the agent according to the invention is preferably in the form of a cream or gel, particularly a gel.

In this regard it is preferred when gas bubbles are incorporated into the inventive cream or into the inventive gel. These gas bubbles are visible to the human eye. Air, nitrogen, oxygen, carbon dioxide, dinitrogen monoxide, argon are exemplary suitable as the gases.

The viscosity of agents in the form of creams or gels is preferably from 10,000 to 500,000 mPas, particularly preferably from 30,000 to 300,000 mPas (each measured with Brookfield RVDV II+ with Heilpath, Spindle T-E, 5 rpm, 20° C.).

If the agent is in the form of a gel, then it is particularly preferably a transparent gel.

A second subject matter of the invention is the use of the agent for the temporary shaping of hair and/or for hair care.

Agents and products containing these agents, especially hair gels or hair creams, lend to treated hair a very strong, long-lasting hold to the hairstyle, while keeping the hair flexible. If the agent is a hair gel, then the gel has a pasty consistency that nevertheless can be uniformly dispersed on the hair without any dripping.

It is inventively preferred to use the agent of the first subject matter of the invention as a leave-on hair treatment agent.

A third subject matter of the invention is a method for treating keratin-containing fibers, especially human hair, wherein an inventive agent of the first subject matter is applied onto the keratin-containing fibers.

It is inventively preferred when keratin-containing fibers are styled before, during or after application of the agent according to the invention.

Furthermore, it is inventively preferred in the context of the method according to the invention not to rinse out the agent from the keratin-containing fibers.

The following examples are intended to illustrate the subject matter of the present invention in more detail, without limiting it in any way.

EXAMPLES

Unless otherwise stated, the quantities are understood to be in weight percent.

1.0 Formulations—

Styling gels A to E according to the following Table were manufactured.

| Raw Materials | A | B | C | D | E |
|---|---|---|---|---|---|
| | Comparative | | Inventive | | |
| Benzophenone-4 | 0.05 | 0.05 | — | — | — |
| Synthalen K [1] | 0.40 | — | — | — | — |
| Neolone PE [2] | 0.50 | 0.50 | — | — | — |
| Disodium EDTA | 0.05 | 0.05 | 0.05 | 0.05 | 0.05 |
| Sorbitol | 3.00 | 3.00 | 3.00 | 3.00 | 3.00 |
| D-Panthenol | 0.15 | 0.15 | 0.15 | 0.15 | 0.15 |
| Neutral TE [3] | 0.50 | 0.50 | — | — | — |
| Aquastyle ® 300 [4] | 10.00 | 10.00 | 7.00 | 9.00 | 7.00 |
| Aculyn 28 [5] | — | — | 6.00 | 6.00 | — |
| Aculyn 88 [6] | — | — | — | — | 6.00 |
| Luviskol VA 64 W [7] | — | — | 5.00 | — | 5.00 |
| PEG-40 hydrogenated castor oil | 0.55 | 0.55 | 0.55 | 0.55 | 0.55 |
| Uvinul P 25 [8] | — | — | 0.10 | 0.10 | 0.10 |
| 2-Phenoxyethanol | — | — | 0.60 | 0.60 | 0.60 |
| Carbopol Ultrez 21 [9] | — | 0.30 | — | — | — |
| Perfume | 0.10 | 0.10 | 0.10 | 0.10 | 0.10 |
| Water | ad 100 | ad 100 | ad 100 | ad 100 | ad 100 |

[1] Polyacrylic acid (ca. 89% active substance content; INCI name: Carbomer) (3V Sigma)
[2] Solution of ca. 2 wt. % 2-methyl-4-isothiazolin-3-one in ca. 83.5 wt. % phenoxyethanol, 12.5 wt. % propane-1,2-diol and ca. 2 wt. % water (INCI name: Phenoxyethanol, Methylisothiazolinone) (Rohm & Haas),
[3] N,N,N',N',-Tetrakis-(2-hydroxypropyl)ethylenediamine (INCI name: Tetrahydroxypropyl Ethylenediamine) (BASF)
[4] Copolymer of N-vinyl pyrrolidone/N-vinyl caprolactam/N-(3-dimethylaminopropyl) methacrylamide and 3-(methacryloylamino)propyl-lauryl-dimethylammonium chloride (active substance 30 wt. % in water/ethanol, INCI name: Polyquaternium-69) (ISP),
[5] Copolymer of (meth)acrylic acid, (meth)acrylic acid esters and Beheneth-25-methacrylic acid ester (19-21 wt. % solids in water; INCI name: Acrylates/Beheneth-25 Methacrylate Copolymer) (Rohm und Haas),
[6] Crosslinked, amphiphilic, anionic polymer (28 to 30 wt. % conc. dispersion in water, INCI name Acrylates/Steareth-20 Methacrylate Crosspolymer) (Rohm & Haas)
[7] Copolymer of vinyl acetate and N-vinyl pyrrolidone in the ratio 40 to 60 (50% active substance in water, INCI name: VP/VA Copolymer) (BASF)
[8] 1,4-Ethoxylated (25 EO) ethyl aminobenzoate (INCI name: PEG25 PABA) (BASF)
[9] Crosslinked acrylic acid copolymer, white powder (INCI name: Acrylates/C10-30 Alkylacrylate Crosspolymer) (Noveon).

Comparative formulations A and B were turbid.

The inventive formulations C, D and E were clear and transparent gels. Air bubbles could be incorporated in a storage stable manner. Excellent shape stabilization was achieved on application onto human hair.

We claim:

1. A styling gel for treating keratin-containing fibers comprising in a cosmetically acceptable carrier: (a) at least one amphiphilic, cationic polymer having at least one structural unit of Formula (I), at least one structural unit of Formula (II), at least one structural unit of Formula (III), and at least one structural unit of Formula (IV),

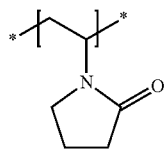
(I)

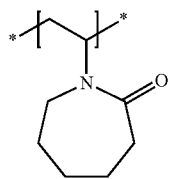
(II)

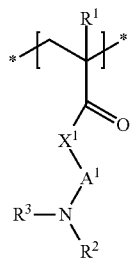
(III)

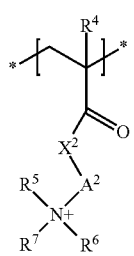
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is for a ($C_8$ to $C_{30}$) alkyl group, and (b) at least one crosslinked amphiphilic, anionic polymer having at least one structural unit of Formula (V) and at least one structural unit of Formula (VI),

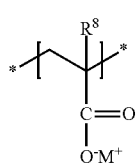
(V)

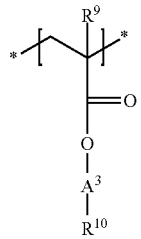
(VI)

wherein $R^8$ and $R^9$ are, independently of one another, a hydrogen atom or a methyl group, $R^{10}$ is $—(CH_2)_{17}CH_3—$, $M^+$ is one equivalent of a physiologically acceptable cation, and $A^3$ is $*—(CH_2CH_2O)_x—*$ wherein x is 20, $*—(CH_2CHMeO)_y—*$ wherein y is a whole number from 5 to 35, or $*—(CH_2CH_2O)_x—(CH_2CHMeO)_y—*$ wherein the sum x+y is a whole number from 5 to 35 and x and y are greater than zero; and wherein the styling get is a transparent gel incorporated in a storage stable form with gas bubbles.

2. The styling gel according to claim 1 wherein $A^1$ and $A^2$ are, independently of one another, ethane-1,2-diyl or propane-1,3-diyl.

3. The styling gel according to claim 1 wherein $R^2$, $R^3$, $R^5$ and $R^6$ are, independently of one another, methyl or ethyl.

4. The styling gel according to claim 1 wherein $R^7$ is decyl, undecyl, dodecyl, tridecyl, tetradecyl, hexadecyl, octadecyl, eicosyl or docosyl.

5. The styling gel according to claim 1 wherein the amphiphilic, cationic polymer is chosen from at least one polymer having at least one structural unit of Formula (I), at least one structural unit of Formula (II), at least one structural unit of Formula (III-8) and at least one structural unit of Formula (IV-8),

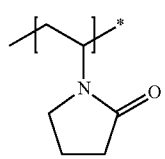
(I)

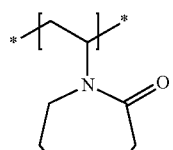
(II)

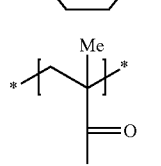
(III-8)

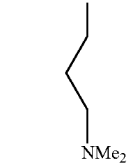

-continued

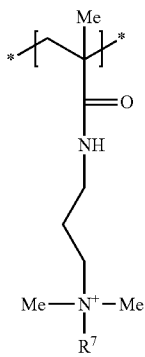
(IV-8)

wherein R⁷ is a ($C_8$ to $C_{30}$) alkyl group.

6. The styling gel according to claim 1 wherein the amphiphilic, cationic polymers (a) are present in an amount of 0.05 wt. % to 15.0 wt. %, based on total weight of the styling gel.

7. The styling gel according to claim 1 wherein the amphiphilic, anionic polymers (b) are present in an amount of 0.05 wt. % to 10.0 wt. %, based on total weight of the styling gel.

8. The styling gel according to claim 1 wherein the amphiphilic, cationic polymers (a) and the amphiphilic, anionic polymers (b) are present in a weight ratio of 1 to 10 to 10 to 1.

9. The styling gel according to claim 1 wherein the amphiphilic, anionic polymers (b) are chosen from copolymers b1 having at least one structural unit according to Formula (V-1), at least one structural unit according to Formula (V-2), and at least one structural unit according to Formula (VI)

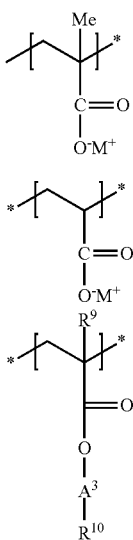
(V-1)
(V-2)

wherein $M^+$ are, independently of one another, a physiologically acceptable cation, $R^9$ is a hydrogen atom or a methyl group, $A^3$ is *—$(CH_2CH_2O)_x$—* wherein x is 20, *—$(CH_2CHMeO)_y$—* wherein y is a whole number from 5 to 35, or *—$(CH_2CH_2O)_x$—$(CH_2CHMeO)_y$—* wherein the sum x+y is a whole number from 5 to 35, and x and y are greater than zero.

10. The styling gel according to claim 1 wherein the amphiphilic, anionic polymers (b) are chosen from Formula (b1-1),

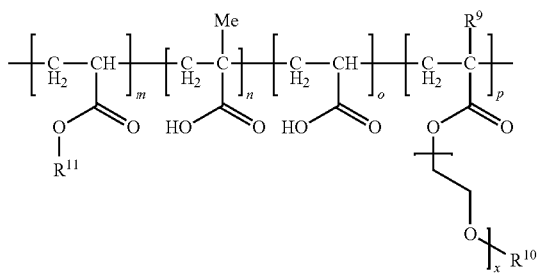
(b1-1)

wherein m, n, o and p are each a whole number greater than zero, $R^9$ is a hydrogen atom or a methyl group, $R^{11}$ is a ($C_1$ to $C_4$) alkyl group, x is 20.

11. The styling gel according to claim 1 further comprising a film-forming and/or setting polymer.

12. The styling gel according to claim 11 wherein the film-forming and/or setting polymer is present in an amount of 0.01 wt. % to 20 wt. %, based on total weight of the styling gel.

13. The styling gel according to claim 1 further comprising at least one surfactant.

14. The styling gel according to claim 13 wherein the at least one surfactant is present in an amount of 0.01 wt. % to 5.0 wt. %, based on total weight of the styling gel.

15. The styling gel according to claim 1 further comprising at least one silicone oil and/or at least one silicone gum.

16. The styling gel according to claim 1 further comprising at least one alkanolamine.

17. The styling gel according to claim 1 wherein the amphiphilic, anionic polymers (b) are present in an amount of 6.0 wt. %, based on total weight of the styling gel.

18. Method for treating keratin-containing fibers comprising applying the styling gel according to claim 1 onto the keratin-containing fibers.

* * * * *